US011280603B2

(12) United States Patent
Kinrot et al.

(10) Patent No.: US 11,280,603 B2
(45) Date of Patent: Mar. 22, 2022

(54) OPTICAL SYSTEMS AND METHODS FOR MEASURING ROTATIONAL MOVEMENT

(71) Applicant: OTM TECHNOLOGIES LTD., Ra'anana (IL)

(72) Inventors: Opher Kinrot, Ra'anana (IL); Uri Kinrot, Hod Hasharon (IL); Arnon Levy, Ra'anana (IL)

(73) Assignee: OTM TECHNOLOGIES LTD., Ra'anana (IL)

( * ) Notice: Subject to any disclaimer, the term of this patent is extended or adjusted under 35 U.S.C. 154(b) by 0 days.

(21) Appl. No.: 16/633,117

(22) PCT Filed: Aug. 1, 2018

(86) PCT No.: PCT/IB2018/001059
§ 371 (c)(1),
(2) Date: Jan. 22, 2020

(87) PCT Pub. No.: WO2019/025871
PCT Pub. Date: Feb. 7, 2019

(65) Prior Publication Data
US 2020/0149864 A1 May 14, 2020

Related U.S. Application Data

(60) Provisional application No. 62/551,355, filed on Aug. 29, 2017, provisional application No. 62/539,651, filed on Aug. 1, 2017.

(51) Int. Cl.
*G01B 9/02* (2006.01)
*G01B 9/02017* (2022.01)
(Continued)

(52) U.S. Cl.
CPC ....... *G01B 9/02041* (2013.01); *G01B 9/0209* (2013.01); *G01B 9/02021* (2013.01);
(Continued)

(58) Field of Classification Search
CPC ............ G01B 9/02041; G01B 9/02021; G01B 9/0209; G01B 2290/45; G01B 2290/70; G02B 27/0172; A61B 3/102; A61B 3/116
See application file for complete search history.

(56) References Cited

U.S. PATENT DOCUMENTS

2006/0077396 A1  4/2006 Park
2010/0149073 A1* 6/2010 Chaum .............. G02B 27/0172
345/8
(Continued)

FOREIGN PATENT DOCUMENTS

WO   WO 2017/096241   6/2017

OTHER PUBLICATIONS

PCT International Search Report of Inter'l Application No. PCT/IB18/01059, dated Dec. 13, 2018, 2 pages.

*Primary Examiner* — Jonathan M Hansen
(74) *Attorney, Agent, or Firm* — Finnegan, Henderson, Farabow, Garrett & Dunner LLP

(57) ABSTRACT

Interferometric systems and methods for measuring rotational movement are described. In one implementation, an interferometer for measuring rotational movement includes a housing and a light source within the housing configured to project coherent light toward a non-coded surface of an object. The interferometer further includes at least one optical element configured to modify the projected coherent light in a manner accounting for a rotation of the object. The interferometer also includes at least one sensor within the housing including at least one light detector configured to detect reflections of the modified projected coherent light from the opposing non-coded surface as the object rotates relative to the housing. The interferometer further includes at least one processor configured to receive input from the at
(Continued)

least one sensor and determine an amount of rotation of the object around the at least one rotational axis.

23 Claims, 13 Drawing Sheets

(51) Int. Cl.
    *G01B 9/0209*     (2022.01)
    *G02B 27/01*     (2006.01)
    *G06F 3/01*     (2006.01)

(52) U.S. Cl.
    CPC ......... *G02B 27/0172* (2013.01); *G06F 3/013* (2013.01); *G01B 2290/45* (2013.01); *G01B 2290/70* (2013.01)

(56) References Cited

U.S. PATENT DOCUMENTS

| | | |
|---|---|---|
| 2010/0182610 A1* | 7/2010 | Utsunomiya ...... G01B 9/02077 356/498 |
| 2011/0237999 A1 | 9/2011 | Muller et al. |
| 2012/0293772 A1 | 11/2012 | Vogler et al. |
| 2017/0105618 A1 | 4/2017 | Schmoll et al. |
| 2017/0206412 A1 | 7/2017 | Kaehler |

\* cited by examiner

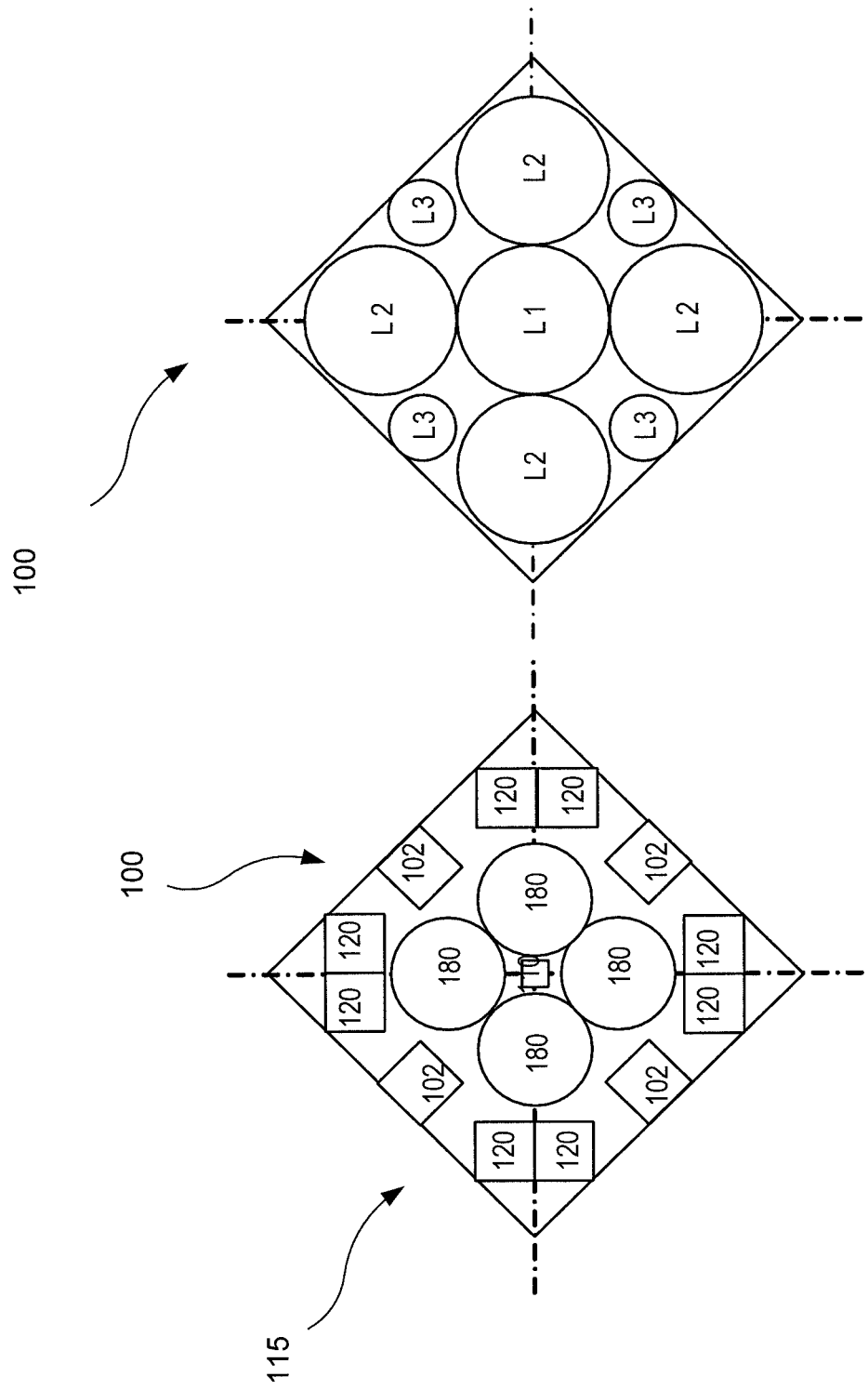

OPTICAL SYSTEMS AND METHODS FOR MEASURING ROTATIONAL MOVEMENT

CROSS-REFERENCE TO RELATED APPLICATIONS

This application claims the benefit of priority of U.S. Provisional Patent Application No. 62/539,651, filed on Aug. 1, 2017, and U.S. Provisional Patent Application No. 62/551,355, filed on Aug. 29, 2017. All of the foregoing applications are incorporated herein by reference in their entireties.

BACKGROUND

Technical Field

The present disclosure generally relates to the field of coherent optical systems and methods. More particularly, and without limitation, the disclosed embodiments relate to interferometric systems and methods for measuring rotational movement of an object.

Background Description

Accurate and fast optical tracking of rotational movement of an object is desired in many areas. For instance, in augmented reality (AR) and virtual reality (VR) applications, optical tracking can be used to track eye movements of a person and measure the gaze direction of a person who is looking at a particular point in space or on a display. Challenges that often exist with such systems involve inaccuracies due to head movement, tracker over-sensitivity, calibration issues, and cost. Some tracking systems even restrict the user's head positions within a narrow area to improve reliability. Thus, there is a need for accurate, robust, and affordable eye tracking technology.

SUMMARY

According to an exemplary embodiment of the present disclosure, an interferometer for measuring rotational movement of an object, such as an eye, is described. The interferometer may include a housing. The interferometer may also include a light source within the housing. The light source may be configured to project coherent light toward an opposing non-coded surface of a spherical object configured to rotate about at least one rotational axis. The interferometer may include at least one optical element configured to modify the projected coherent light in a manner accounting for a rotation of the spherical object. The interferometer may also include at least one sensor within the housing including at least one light detector configured to detect reflections of the modified projected coherent light from the opposing non-coded surface as the spherical object rotates relative to the housing. The interferometer may further include at least one processor configured to receive input from the at least one sensor and determine an amount of rotation of the spherical object around the at least one rotational axis.

According to a further exemplary embodiment of the present disclosure, a head-mounted display device is described. The device may include a housing. The device may also include a light source within the housing configured to project coherent light toward an eye of a user wearing the device. The device may further include at least one optical element configured to modify the projected coherent light in a manner accounting for a rotation of the eye. The device may also include at least one sensor. The at least one sensor may include at least two pairs of light detectors and configured to detect reflections of the modified projected coherent light from the eye as the eye rotates. The device may further include a memory configured to store a resting position of the eye and at least one processor. The at least one processor may be configured to display content to the user, determine an amount of rotation of the eye around the at least one rotational axis based on a relative phase difference between the detected reflections and internal reference beams, identify a position of the eye relative to the resting position, and change the content displayed to the user in response to the identified position of the eye of the user wearing the device.

According to a yet further exemplary embodiment of the present disclosure, a method for measuring rotational movement is described. The method may include projecting coherent light toward an opposing non-coded surface of an object configured to rotate about at least one rotational axis. The method may also include splitting the projected coherent light into a plurality of internal reference beams. Each internal reference beam may be associated with a different direction. The method may further include modifying the projected coherent light in a manner accounting for a rotation of the object. The method may include detecting reflections of the modified projected coherent light from the opposing non-coded surface as the object rotates; modifying the detected reflection in a manner accounting for a rotation of the object; and determining an amount of rotation of the object around the at least one rotational axis based on a relative phase difference between the detected reflections and the internal reference beams.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims. It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 5B is a schematic horizontal cross-sectional representation of the exemplary interferometer of FIG. 5A.

FIG. 5C is another schematic horizontal cross-sectional representation of the exemplary interferometer of FIG. 5A.

DETAILED DESCRIPTION

Figure 1:
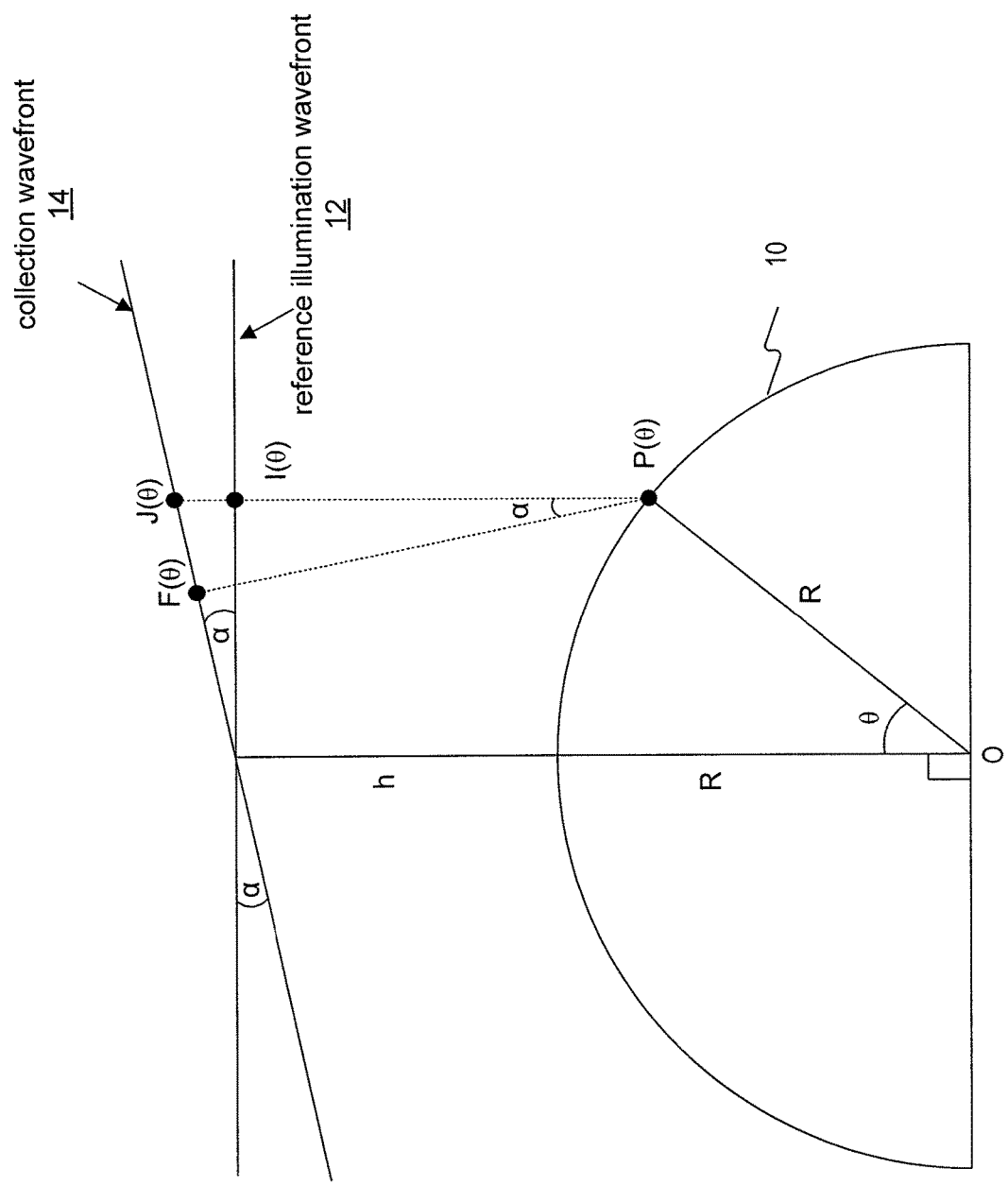
FIG. 1 graphically illustrates an optical model for measuring rotation of an object using an interferometer.

Reference will now be made in detail to embodiments and aspects of the present disclosure, examples of which are illustrated in the accompanying drawings. Where possible, the same reference numbers will be used throughout the drawings to refer to the same or like parts. The disclosure is not limited to the described embodiments and examples. Instead, the proper scope is defined by the appended claims.

The disclosed embodiments relate to systems and methods for measuring rotational movement of an object. The disclosed embodiments may involve an interferometer. As used herein, the term "interferometer" broadly includes any device or system that utilizes the interference of beams of light to determine information, such as information indicative of the movement of an object. By way of example only, the interferometer may be included in a display device, such as a VR headset or AR headset. Advantageously, embodiments of the present disclosure allow for tracking of fast rotational movement of an object of any shape at a suitable working distance from the object. In some embodiments, the working distance may be preferably short, such a best performance of the interferometer may be obtained when the object is close to the interferometer and the maximum working distance is equal to or less than about 10 times of the diameter of the interferometer's illumination beam at the exit of the interferometer. In other embodiments, the working distance may be predefined, and may be greater than about 10 times of the diameter of the interferometer's illumination beam at the exit of the interferometer. For example, the working distance may be between 10 times to 30 times, between 15 times to 50 times, or between 20 times to 100 times of the diameter of the illumination beam at the exit of the interferometer. As described herein, the illumination beam may be a focusing or collimated laser beam.

Optical Model for Measuring Rotation Using an Interferometer

It is contemplated that using an interferometer for eye tracking may provide one or more benefits, including an ability to accurately track fast eye movements, such as saccades, insensitivity to ambient light, such as light from AR and VR displays, insensitivity to tear films, an ability to track movement of the sclera and iris, and an ability to detect blinks. Interferometers can be designed for measuring linear translational movement of a diffusely reflective object or a diffusely reflective surface, as described in Applicant's U.S. Pat. No. 6,741,335 (the '335 patent). The diffusely reflective surface is modeled as a group of random reflectors moving together by being part of the same solid object. The surface may be illuminated using a plane wave and a reflected plane wave may be collected and combined with a reference illumination plane wave in a direction offset from the illumination direction. The resulting interference signal may contain beats related to the linear translation of the surface. When using the known OTM interferometers as described in the '335 patent, the phase difference between the illumination plane wavefront and the collection plane wavefront due to linear translation of the surface needs to be substantially the same for all of the random reflectors on the surface. Additional details regarding the usage and characteristics of other example interferometers that are consistent with some embodiments of the suggested sensor are included in the '335 patent, International Publication No. PCT/IB2016/000096, and International Publication No. PCT/IB2017/000617 which are incorporated herein by reference in their entirety.

With certain modifications, the interferometer may be used to measure rotational movement. For example, in the '335 patent, the suggested interferometer is used to measure the rotational angle of a cylinder. However, to obtain accurate measurement, the phase difference for all the reflectors on the surface of the cylinder may need to be the same. In the '335 patent, this was achieved by using specially sized optical elements. For example, to measure the rotation of a rotating shaft, with reference to FIGS. 20A and 20B, the '335 patent describes the use of a one-dimensional curved grating whose diameter is matched to the diameter of the shaft and whose lines are parallel to the shaft axis. A light source focuses onto the centerline of the shaft such that its phase is constant across the grating. A detector detects the reflected light from the surface of the shaft and the reference light reflected from the grating. As shown in FIGS. 20A and 20B in the '335 patent, the light source and detector are at the circumferential position with respect to the shaft but are axially offset from each other. Such configuration may work only when an amplitude grating ($0^{th}$ order) is placed within the Fresnel distance, i.e., on the order of the grating pitch (a few micrometers), to the rotating shaft. The use of the amplitude grating with a matching diameter and its restriction to be placed within the Fresnel distance to the object to be measured may limit the use of the OTM interferometer as described in the '335 patent for measuring rotational movement.

It may be possible to use an OTM interferometer to measure rotational movement without using the specially sized optical elements, such as the amplitude grating, at a distance away from the object to be measured. However, it may require substantially reducing the diameter of the illumination beam as explained below with reference to FIG. 1.

In a typical OTM interferometer, such as described in the '335 patent, the illumination and reflection beams may both be plane waves. To obtain accurate movement measurement, the accumulated phase difference for all the illuminated reflectors on the surface of the measured object may need to be substantially the same. FIG. 1 graphically illustrates an optical model for measuring rotation of a spherical object 10 having a radius R and rotating around axis O using a typical OTM interferometer. As shown in FIG. 1, assuming the illumination wavefront is parallel to the horizontal axis and taking the illumination wavefront at height R+h as a reference illumination wavefront 12, let $P(\theta)$ be the point on the sphere the radius to which forms an angle $\theta$ to the vertical axis. The distance of $P(\theta)$ to the point $I(\theta)$ on the reference illumination wavefront is $h+R(1-\cos(\theta))$. Assuming a collection wavefront 14 is at an angle $\alpha$ to the illumination wavefront, the distance from point $P(\theta)$ to point $F(\theta)$ on the collection wavefront is the distance from point $P(\theta)$ to point $J(\theta)$ times $\cos(\alpha)$, which is equal to $(h+R*(1-\cos(\theta))+R*\sin(\theta)*\tan(\alpha))*\cos(\alpha)$. Thus, the total distance $L(\theta)$ from reference illumination wavefront 12 to collection wavefront 14 is the sum of the distance between point $P(\theta)$ and point $F(\theta)$ and the distance between $P(\theta)$ and point $I(\theta)$, where $L(\Theta)= ((h+R*(1-\cos(\theta))*(1+\cos(\alpha))+R*\sin(\alpha)*\sin(\theta)$. Thus $dL(\theta)/d\theta=R*(1+\cos(\alpha))*\sin(\theta)+R*\sin(\alpha)*\cos(\theta)$ the derivative of which with respect to $\theta$ is $dL^2(\theta)/(d\theta)^2=R*(1+\cos(\alpha))*\cos(\theta)-R*\sin(\alpha)*\sin(\theta)$. This second derivative is bound in absolute value for $\theta<\pi/2$ by the value $2*R*\cos(\theta)$ obtained when $\alpha$ is zero.

To achieve substantially uniform phase change accumulation across all the reflectors on the surface of object 10, the above second derivative with respect to $\theta$ may need to be relatively small. Thus, the center of the illuminated area on object 10 may need to have large enough $\theta$ such that $\cos(\theta)$ is relatively small. Greater $\theta$ results in a smaller $dL(\theta)/d\theta$, which renders a smaller signal. This is because in this one-dimensional analysis, the energy of illumination is also proportional to $\cos(\theta)$ Also, the illuminated area of the surface of object 10 may need to be small enough so that $\theta$ does not vary much such that the phase difference of the reflectors within the illuminated area does not vary much. Here, for example, assuming an exemplary object having a radius of 12 mm, $\alpha$ set to 0.1 radians, when locating the sensor at $\theta=\pi/4$, the size of the illumination beam needs to be reduced to approximately 70 μm to obtain a maximum difference of about 0.5% between the values of the first derivatives for different locations or about 0.5% accumulated phase difference between reflectors on the sphere. Because, as mentioned above, in a typical OTM interferometer the illumination and reflection beams are plane waves, an illumination beam diameter of 70 μm with illumination wavelength of 1 μm would diffract after travelling for a very short distance, such as 5 mm. Thus, using a typical OTM sensor with plane wave illumination for accurate rotation measurement would be impractical as it requires both a very small beam size and a very short working distance. Thus, the specific embodiments of the interferometer described in the '335 patent may not be used for directly measuring the rotational movement or other movements which are substantially not linear translations.

Optical Models for Measuring Rotation using an Interferometer Consistent with the Present Disclosure Embodiments of the present disclosure may provide an interferometer that allows measuring rotational movement of an object of any desired shape at a suitable working distance. The working distance may be relatively short, such as shorter than about 10 times of the diameter of the illumination beam at the exit of the interferometer. The working distance may be relatively long and predefined, such as longer than about 10 about 10 times of the diameter of the illumination beam at the exit of the interferometer. It is contemplated that to achieve accurate measurement of a given type of movement, a condition may be desired where the total phase change accumulated from the illumination wavefront to the collected wavefront is about the same non-zero amount for all reflectors on the surface of the object. It is further contemplated that the illumination wavefront and the collection wavefront can be adjusted to satisfy this condition, thereby improving signal quality and measurement accuracy for extracting movement information. In some embodiments, the illumination and collection wavefronts can be adjusted separately. For example, the illumination wavefront can be adjusted such that each reflector on the surface of the object is illuminated with about the same phase. Also, the collected wavefront can be adjusted such that the phase change for each reflector on the surface of the object is about the same as the object rotates.

Embodiments of the present disclosure provide an interferometer that may satisfy the above-described condition for measuring the rotational movement of an object, such as a spherical object or a cylindrical object, at a working distance away from the surface of the object. The working distance may be substantially longer than the Fresnel distance, which is typically not more than a few tens of microns.

According to one aspect of the present disclosure, when the object rotates around a center of rotation in two independent directions of rotation (such as a sphere around its center), a spherical wave converging to the center of rotation of the object may be used to illuminate the object. The spherical wave may allow each reflector on the surface of the object to be illuminated with the same phase as the object rotates such that the reflectors do not accumulate relative phase difference due to the object's rotation.

According to another aspect of the present disclosure, when the object rotates around a single axis, such as a rotating shaft or cylindroid, the illumination wavefront may be a cylindrical wavefront obtained by using a cylindrical lens placed after an illumination plane wave. The cylindrical wavefront may be focused to the centerline of the shaft or to a line that is laterally offset from the centerline of the shaft.

As a non-limiting example, to measure the rotational movement of a spherical object at a working distance away from the surface of the spherical object, an illumination beam with a relatively large diameter and a focal length substantially equal to the sum of the working distance and the radius of the spherical object can be used. In some embodiments, the illumination beam may be focused to the center of rotation of the spherical object. In other embodiments, the illumination beam may be focused to a point that is laterally offset from the center of rotation of the spherical object.

According to the present disclosure, a spherical wave reflected from a spherical object with a center at the center of rotation of the spherical object may be collected. The collection of a spherical wave allows the phase change for each reflector on the surface of the spherical object to be substantially zero. It is contemplated that when the collection spherical wave has a focus at the center of rotation of the object, the illumination spherical wave may need to be focused at an offset from the center of rotation. This is because if the illumination spherical wave may also be focused at the center of rotation, as the spherical object rotates, the overall phase accumulation across all reflectors on the surface of the object would be substantially zero. This is similar to a translational measurement of a plane where the directions of the illumination and collection plane waves are perpendicular to the surface, providing no overall phase accumulation.

Consistent with embodiments of the present disclosure, to obtain a non-zero phase change accumulation from the rotation of the object, at least one of the illumination spherical beam and the collection spherical beam may have a center that does not coincide with the center of rotation of the object. In some embodiments, an illumination spherical wave with a center at the center of rotation of the spherical object is used to illuminate the surface of a spherical object and a reflected spherical wave with a focus at a point laterally offset from the center of rotation is collected. Alternatively, an illumination spherical wave with a focus at a point laterally offset from the center of rotation of a spherical object may be used to illuminate the surface of the spherical object and a reflected spherical wave with a focus at the center of rotation is collected. Yet alternatively, an illumination spherical wave with a focus at a point laterally offset from the center of rotation of a spherical object may be used to illuminate the surface of the spherical object and a reflected spherical wave with a focus at an offset from the center of rotation of the spherical object different from the offset of the illumination spherical wave is collected. As another non-limiting example, an illumination cylindrical wave that focuses onto the centerline of a cylindrical object is used to illuminate the surface of the cylindrical object, such as a shaft, and a reflected spherical wave that originates from a line parallel to and laterally offset from the centerline is collected. Alternatively, an illumination cylindrical wave that focuses onto a line parallel to and laterally offset from the centerline of a cylindrical object is used to illuminate the surface of the cylindrical object, such as a shaft, and a reflected cylindrical wave that originates from the centerline is collected. Yet alternatively, an illumination cylindrical wave with a focus at a line laterally offset from the centerline of rotation of a cylindrical object may be used to illuminate the surface of the cylindrical object and a reflected cylindrical wave with a focus at an offset from the centerline of rotation of the cylindrical object different from the offset of the illumination cylindrical wave is collected.

As described herein, a point laterally offset from the center of rotation of the spherical object refers to a point near the center of rotation and located at about the same distance away from a detector for detecting the reflected wave from the object or from a lens for collecting the reflected wave from the object. Also, a line parallel to and laterally offset from the centerline of the cylindrical object refers to a line parallel to and near the centerline and located at about the same distance away from a detector for detecting the reflected wave from the object or from a lens for collecting the reflected wave from the object.

According to one aspect of the present disclosure, when the object is a spheroid, a spherical illumination wave may be obtained by using a focusing lens, such as a spherical lens or an aspherical lens, after an illumination plane wave. A spherical collection wave may be received and converted to a reflection plane wave by a collection lens similar or identical to the optical lens used for illumination. In some embodiments, the focusing lens and the collection lens may be one optical lens. In other embodiments, the collection lens is a separate lens and located adjacent the focusing lens. As described herein, the focal length of the illumination beam may be equal to the focal length of the lens that is used to converge an illumination plane wave. Also, the focal length of the reflection beam may be equal to the focal length of the lens that is used to collect and collimate the reflection beam. The interference of the resulting reflection plane wave with a reference plane wave allows for obtaining an accurate measurement of the rotational movement of the spheroid.

In some embodiments, the interferometer may allow for measuring the rotational movement of a spherical object in two dimensions. The interferometer may further allow for measuring translational movement of the spherical object away from or towards a detector. Additionally, or alternatively, the interferometer consistent with embodiments of the present disclosure may also allow for measuring the rotational movement of a cylindrical object, such as shaft, translational movement of the cylindrical object towards and away from the detector, and linear movement of the cylindrical object along its axis. In some embodiments, at least three collection lenses can be used to collect at least three reflection beams from at least three non-collinear collection directions. As a non-limiting example, when three collection lenses are used to collect three reflected beams from a spherical object, the focal points of the three lenses may form a triangle near the center of rotation of the object. As another non-limiting example, when three collection lenses are used to collect three reflected beams from a cylindrical object, the focal points or focal lines of the three lenses may form a triangle by the centerline of the object as imaged in a plane perpendicular to the centerline.

Figure 2:
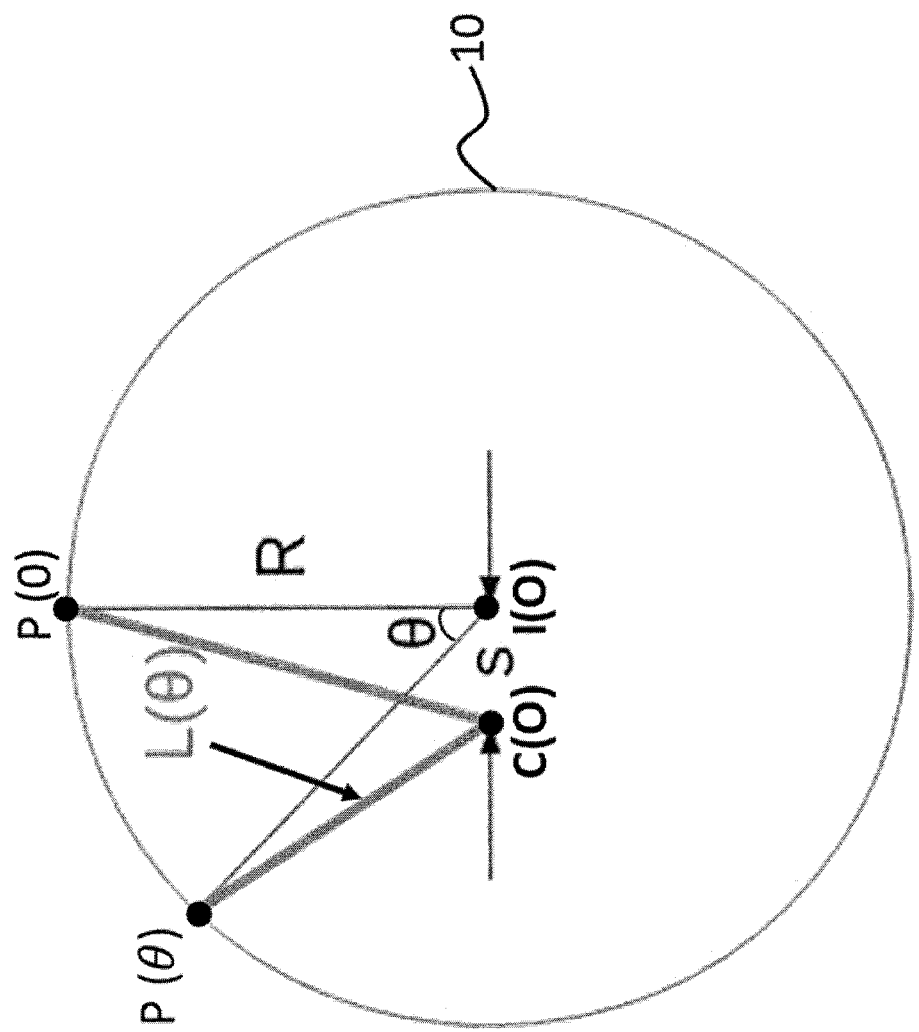
FIG. 2 graphically illustrates another optical model for measuring rotational movement, according to embodiments of the present disclosure.

The following disclosure with reference to FIG. 2 describes an exemplary optical model for measuring phase accumulation of the reflectors on the surface of a rotating spherical object using the interferometer consistent with some embodiments.

As shown in FIG. 2, a cross-section of an exemplary object 10 that has a radius R. Object 10 may be a spherical object or a cylindrical object having a centerline (or an axis of rotation) perpendicular to the plane of the cross-section. Assuming object 10 is illuminated with a spherical wave having a focus I(O) at the center of rotation of object 10, the collection spherical wave has a focus C(O) laterally offset from I(O) by a distance S. As described above, when the illumination spherical wave focuses to the center of rotation of object 10, each reflector on the surface of object 10 may be illuminated with the same phase such that the reflectors do not accumulate relative phase difference due to the object's rotation. When the collection spherical wave is focused at a point offset from the center of rotation, phase accumulation across all reflectors on the surface of the object is approximately linearly proportional to the rotational angle of the object as further described below.

As described herein, the phase accumulation can be similarly obtained where the collection wave rather than the illumination wave has a focus at the center of rotation or when both the illumination wave and the collection wave has a focus offset from the center of rotation. The phase accumulation can also be similarly where the rotational movement of a cylindrical object is measured.

As shown in FIG. 2, P(0) is a point on the surface of object 10 closest to the illumination source. P($\theta$) is another point on the surface of object 10. The radius connecting P($\theta$) and I(O) forms an angle $\theta$ with the radius connecting P(0) and I(O). As described herein, the illumination wavefront may extend from P($\theta_{-m}$) to P($\theta_m$) on the surface of object 10 (not shown). The phase accumulation of a reflector at P($\theta$) is directly proportional to the distance L($\theta$), which is the distance between P($\theta$) and the focal point of the collection wave C(O). Suppose that at t=0, a reflector on the surface of object 10 is at P($\theta$) and a short time, dt, after that, the reflector is moved to P($\theta$+d$\theta$). The change of the distances of the two locations P(θ) and P(θ+dθ) to the focal point C(O) of the collection wavefront is equal to dL(θ)=L(θ+dθ)−L(θ), which is proportional to the phase accumulation of the reflector on the surface of object 10 as it rotates during the time period dt.

The rotational angle of object 10 can be measured based on the phase accumulation of illuminated reflectors on the surface of object 10. Assuming S=k*R, k<1, the cosine law gives L(θ)=R*sqrt(1+k$^2$−2k*sin(θ)) for any θ<π/2. The derivative of L(θ) with respect to θ is proportional to the rate of phase change for an infinitesimal rotation, which is dL(θ)/d θ=R*k*cos(θ)/sqrt(1+k$^2$−2k*sin(θ))=R*k*sqrt((1−sin$^2$(θ))/(1+k$^2$−2k*sin(θ))). Assuming the illumination wavefront extends to θ$_m$ and k=sin(θ$_m$), then dL(θ=θ$_m$)/d θ=R*k. When θ=0, dL(θ=0)/d θ=R*k/sqrt(1+k$^2$)≈R*k*(1−k$^2$/2). For a non-limiting example, when k is equal to 0.1, S is equal to R/10, and θ$_m$ is 0.1 radian, the deviation from linearity for the full extension of the illumination beam amounts to less than 0.5%. It is important to note that since S is a fixed parameter of the design and independent of R, the accumulated phase is linearly dependent on the rotation irrespective of the radius R of the individual reflector (up to the accuracy described previously) dL(θ)/d θ≈R*k=S. Thus, the phase contribution of each reflector in a collection of reflectors with varying distances from the center of rotation is the same. This enables measurement of rotation of objects with varying form, and not necessarily having spherical or rotational symmetry. As described herein, for the total phase accumulation of a reflector to go through a cycle, the rotational angle Δθ of the object needs to roughly satisfy Δθ*dL (θ)/d(θ)=λ, where λ is the wavelength of illumination. It is contemplated that it is desirable to have the phase accumulation across the reflectors in the illuminated area substantially the same for rotational angles that result in phase accumulation of more than one cycle, such as 10 to 60 cycles. The ability to keep the deviation of the linear relationship between the phase change accumulation and rotational angle of the object for the extension of the illumination beam to be less than 1% allows for accurate measurement of the rotation of the object within a fraction of the illumination wavelength.

Exemplary Interferometers for Measuring Rotation

Embodiments of the invention include an interferometer. As used herein the term interferometer may broadly include any device that utilizes the interference of beams of light to determine movement information. Interferometer 100 in FIG. 5 is one example of an interferometer in accordance with embodiments of the invention. An interferometer consistent with embodiments of this disclosure may be configured for measuring rotational movement.

In accordance with the present disclosure an interferometer may include a housing. The housing may have any suitable shape and dimension to contain the components of the interferometer in a limited space. The housing may be part of a device that has the function for measuring rotational movement of an object, such as a paired head-mounted display device. For example, interferometer housing 105 is illustrated schematically in FIG. 5A.

An interferometer for measuring rotational movement in accordance with the present disclosure may further include a light source configured to project coherent light toward an opposing non-coded surface of an object configured to rotate around at least one rotational axis. The light source may include any device configured to emit coherent light having a relatively long coherence length, such as a coherence length greater than twice the working distance, and good spatial coherence, such as single spatial mode emission laser. For example, one type of light source that may be used is a single mode vertical-cavity surface-emitting laser (VCSEL). Another type of light source that may be used is an external cavity diode laser (ECDL). In some examples, the light source may include a laser diode configured to emit light at a wavelength between about 650 nm and about 1000 nm. Alternatively, the light source may include a laser diode configured to emit light at a wavelength between about 800 nm and about 900 nm.

In some embodiments, the light source may be operably connected to a controller that modulates the operational states of the light source. For example, the controller may activate or deactivate the light source, modulate the duration of a pulse of when the light source is a pulsed light source, and/or switch or tune the emission wavelengths of the light source.

The light source may be configured to project coherent light toward an opposing surface of an object. As used herein the term "projecting coherent light" may include radiating a monochromatic wave having a well-defined phase relationship across its wavefront in a defined direction, such as a single spatial mode laser. The interferometer may include optical components for directing the coherent wave of the light source towards an opposing surface of an object located at a working distance away from the distal end of the interferometer. For example, the distal end of the interferometer may be at a working distance of about 25 mm to about 50 mm from the opposing surface of the object. The spot diameter of the projected light or the light beam at the exit of the interferometer may be between about 1 mm to about 5 mm. In one embodiment, the projected light beam may be essentially collimated. In some embodiments, the light projected from the light source may have a coherence length greater than about 10 mm, about 25 mm, about 50 mm, or about 75 mm.

As described herein, the term "surface" may include any type of tangible material, such as a surface made of wood, metal, ceramic, plastic, paper, fabric, glass, crystal, stone, or any other synthetic or natural material. Further, the surface may be biological tissue such as tissues of the cornea, aqueous humor, sclera, iris pupil, blood vessels, lens, choroid, vitreous, retina and the optic nerve, that are part of the eye. The term "non-coded surface" broadly includes any type of tangible material without a predefined pattern. The predefined pattern may include any regularly or irregularly spaced visual indicators forming areas on a surface that may be used as a reference for measuring rotational movement. The term "non-coded surface" as used herein suggest that the use of embodiments of the interferometer for measuring rotation does not rely on any recognizable features on the surface of the object.

As described herein, the term "object" may include any object that has a three-dimensional shape. The projection of the object may have at least one obtuse angle or an arc. As a non-limiting example, the object may be a spherical object having an overall spherical shape or an overall elliptical shape, such as a sphere, a spheroid, an eyeball, an egg-shaped or oval-shaped object. As another non-limiting example, the object may be a cylindrical object having an elongated body and overall circular or elliptical cross-section, such as a cylindroid or a shaft. As another non-limiting example, the object may have any three-dimensional shape, such as a hexagonal prism, a cube, a box, or an object of an irregular shape. As described herein, when the object is a spherical object, such as a sphere or a spheroid, the object may be rotated about a plurality of rotational axes.

When the object is a cylindrical object, such as a cylindroid or a shaft, the object may be rotated about a single rotational axis, such as the centerline.

An interferometer for measuring rotational movement in accordance with the present disclosure may further include at least one optical element configured to modify the projected light in a manner accounting for a rotation of the object. In some embodiments, the at least one optical element may include a focusing lens located at a predetermined working distance from the surface of the object. The focusing lens may have a focal length corresponding to the working distance. As a non-limiting example, the focal length of the focusing lens may be equal to the sum of the working distance and the radius of rotation of the object.

Figure 5A:
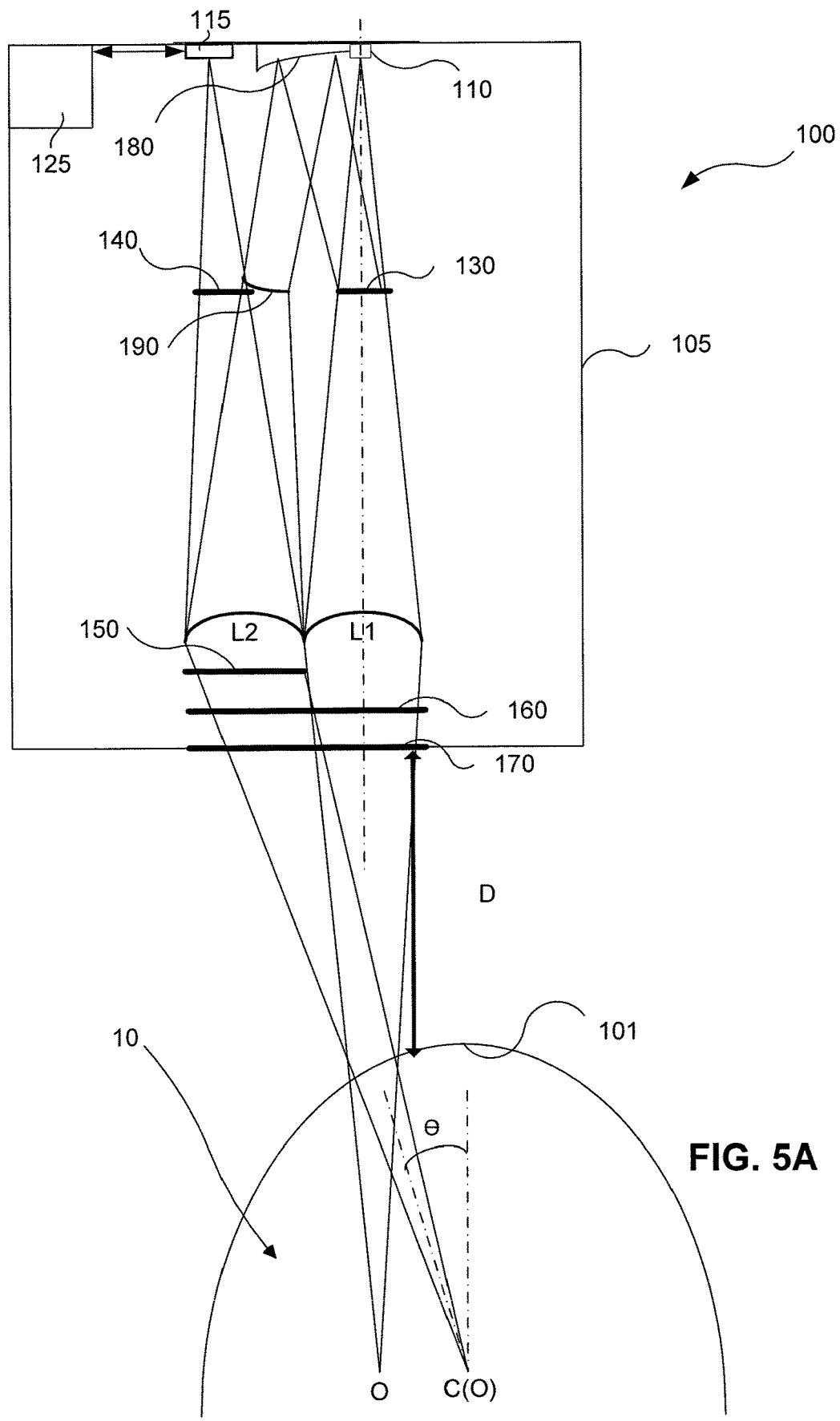
FIG. 5A is a schematic vertical cross-sectional representation of another exemplary interferometer for measuring rotational movement, according to embodiments of the present disclosure.

In some embodiments, the focusing lens may be configured to modify the projected coherent light by forming a spherical illumination wave converging to the center of rotation of the object. In other embodiments, the focusing lens may be a cylindrical lens configured to modify the projected coherent light by forming a cylindrical illumination wave converging to an axis of rotation of a cylindrical object. Lens L1 in FIG. 5A, illustrates one non-limiting example of one embodiment of a focusing lens consistent with the present disclosure, and as is described later in greater detail.

In some embodiments, the at least one optical element may include a beam splitter, such as a diffraction grating, configured to split the projected coherent light into a plurality of internal reference beams, wherein each of the internal reference beams is associated with a different direction. Beam splitter 130 in FIG. 5A, illustrates one non-limiting example of one embodiment of the at least one optical element consistent with the present disclosure, and as is described later in greater detail. The at least one optical element may further be configured to modify reflections of the modified projected coherent light from the non-coded surface of the object such that a resulting interference of the modified reflections with the plurality of internal reference beams is linearly related to the amount of rotation of the object. Diffraction grating 717 in FIG. 7, illustrates another non-limiting example of the at least one optical element consistent with the present disclosure, and as is described later in greater detail.

An interferometer for measuring rotational movement in accordance with the present disclosure may further include at least one sensor. In some embodiments, the sensor may include at least one light detector configured to detect reflections of the modified projected coherent light from the non-coded surface of the object as it rotates relative to the housing. In some embodiments, the at least one sensor includes the light detectors in pairs. The use of pairs of light detectors may allow for the determination of the rotational direction of an object in around a given axis and/or the direction of translational movement of the object. Sensor 115 in FIG. 5A, illustrates one non-limiting example of one embodiment of the sensor consistent with the present disclosure, and as is described later in greater detail.

As described herein, the term "light detector" may include any device configured to measure properties (e.g., power, frequency) of electromagnetic waves and to generate an output relating to the measured properties. In some embodiments, the light detectors may be configured to convert reflections of the coherent light into photocurrents. Each light detector may have a similar construction, or the light detectors may be of differing constructions that are electrically connected or disconnected from each other. For example, the light detectors may be of a different size or a different shape. When more than one light detector is used, the light detectors may be configured to operate independently or collaboratively. The light detectors may be coupled electrically, optically, mechanically or by other means that permit them to interact. Light detector 120 in FIG. 5B, illustrates one non-limiting example of one embodiment of the light detector consistent with the present disclosure, and as is described later in greater detail. As used herein, the term "detecting reflections of the coherent light" may include receiving at least part of the coherent light reflected from the surface of the object, and collecting data associated with the received reflections of the coherent light. The collected data may be provided to a processor so that changes in the photocurrents can be detected by the processor.

As described herein, the interferometer may include or be associated with at least one imaging sensor. The term "imaging sensor" may broadly include any device, element, or system that responds to a physical condition and transmits a signal based on that condition. The imaging sensors may be used for determining reference positions on the surface of the object to be measured. Imaging sensor 102 in FIG. 5B, illustrates one non-limiting example of one embodiment of the imaging sensor consistent with the present disclosure, and as is described later in greater detail.

An interferometer for measuring rotational movement in accordance with the present disclosure may further include at least one processor. The at least one processor may be configured to receive input from the at least one sensor and determine an amount of rotation of the object around at least one rotational axis. For example, the at least one processor may be configured to determine a first amount of rotation of an object around a first rotational axis and a second amount of rotation of the object around a second rotational axis. In some instances, the at least one processor may be configured to determine the amount of rotation of the object without prior knowledge of a radius or a shape of the object. The at least one processor may be further configured to additionally determine an amount of translational movement of the object towards or away from the at least one sensor in addition to the amount of rotation of the object around the at least one rotational axis. Processor 125 in FIG. 5A, illustrates one non-limiting example of one embodiment of the at least one processor consistent with the present disclosure, and as is described later in greater detail.

In some embodiments, the light source may be operably connected to a controller including the at least one processor and a computer-readable medium that stores instructions or operational steps. These instructions or steps, when executed by the processor, modulate the operational states of the light source. For example, the processor may activate or deactivate the light source, modulate the duration of a pulse of a pulsed light source, and/or switch or tune the emission wavelengths of the light source.

As described herein, the at least one processor may constitute any physical device having an electric circuit that performs a logic operation on input or inputs. For example, the at least one processor may include one or more integrated circuits, microchips, microcontrollers, microprocessors, all or part of a central processing unit (CPU), graphics processing unit (GPU), digital signal processor (DSP), field-programmable gate array (FPGA), application specific integrated circuit (ASIC) or other circuits suitable for executing instructions or performing logic operations. The instructions executed by at least one processor may, for example, be pre-loaded into a memory integrated with or embedded into a controller or may be stored in a separate computer-readable medium. The computer-readable medium may be a Random-Access Memory (RAM), a Read-Only Memory (ROM), a hard disk, an optical disk, a magnetic medium, a flash memory, other permanent, fixed, or volatile memory, or any other mechanism capable of storing instructions. In some embodiments, such as in ASIC, the instructions are implemented in logic transistors. In some embodiments, the computer-readable medium is configured to store information representative of the movements of the interferometer or the device housing the interferometer.

In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by any other means that permit them to interact.

In some embodiments, when the object is a spherical object configured to rotate about two orthogonal rotational axes, the at least one processor is further configured to determine a first amount of rotation of the spherical object around the first rotational axis and a second amount of rotation of the spherical object around the second rotational axis based on a non-zero phase change associated with detected reflections of a spherical illumination wave and a plurality of internal reference beams generated by the beam splitter.

In other embodiments, when the object is a cylindrical object configured to rotate about a single rotational axis, the at least one processor may be configured to determine an amount of rotation around the single rotational axis. For example, the at least one processor may be configured to determine the amount of rotation around the single rotational axis based on a non-zero phase change associated with detected reflections of a cylindrical illumination wave and at least one internal reference beam generated by the beam splitter. As described herein, the term "amount of rotation" may refer to the rotational angle of the object around an axis in a given measurement, the rotational speed of the object around a given axis, the angular speed, or the angular frequency of the object around a given axis of rotation.

Exemplary embodiments to be described below in reference to schematic representations of optical systems and/or components are directed to exemplary interferometers consistent with the present disclosure. The schematic representations are to be understood as not being drawn to scale.

Figure 3:
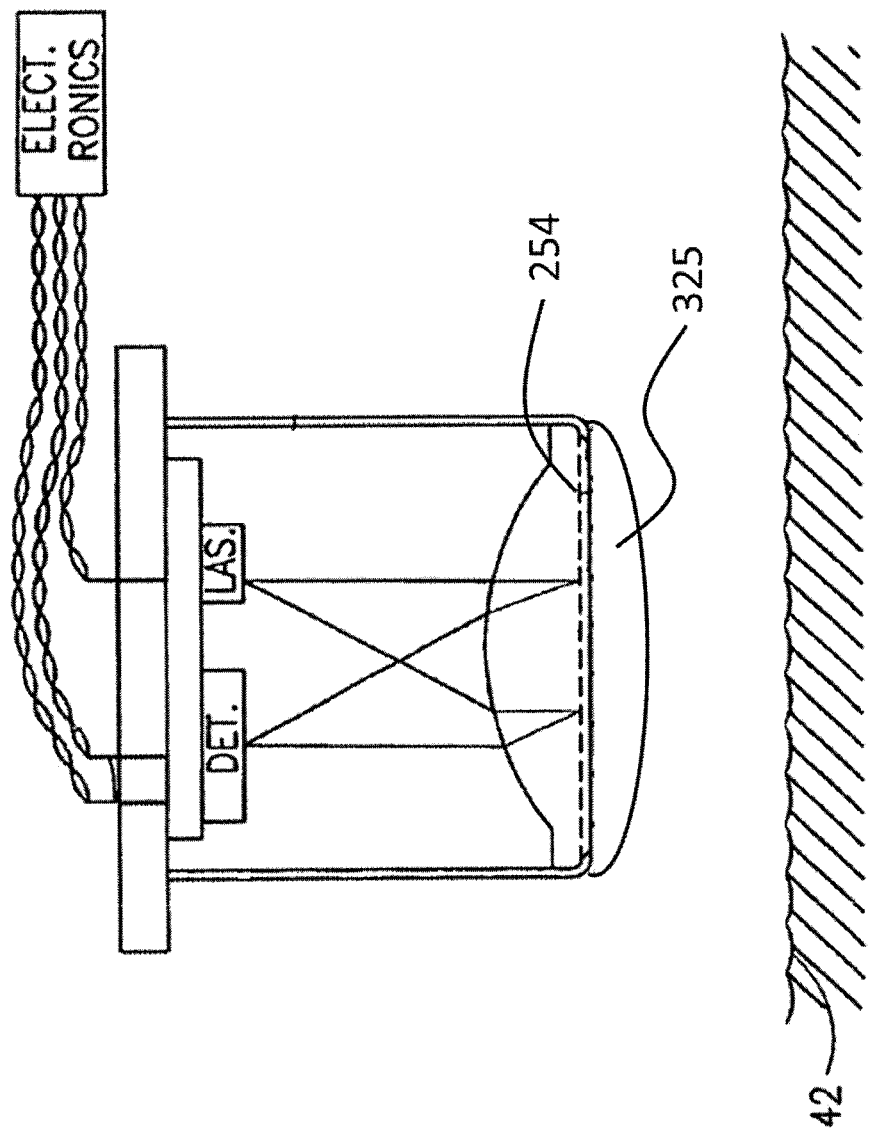
FIG. 3 is a schematic representation of an exemplary interferometer, according to embodiments of the present disclosure.

FIG. 3 is a schematic representation of an exemplary interferometer for measuring rotational movement, according to embodiments of the present disclosure. The exemplary interferometer may be constructed based on FIG. 10 of the '335 patent. Consistent with embodiments of the present disclosure, the interferometer may be modified to measure rotational movement of an object at a working distance. As a non-limiting example, a focusing lens 325 may be placed between grating 254 and surface 42 in order to modify the wavefront. In some instances, when the object is a spherical object, such as a rotating sphere, the focusing lens may be a spherical or aspherical focusing lens with a focal length greater than the rotational radius of the spherical object. In such instances, the focusing lens may convert the illumination plane wave to a spherical wave converging to the center of rotation of the object. The focusing lens may further collect reflected spherical wave from the surface of the object and convert it to a plane wave that interferes with the internal reference illumination plane waves, such as the first order reflections from grating 254, to generate interference signals for obtaining the rotational information of the object. In other instances, when the object is a cylindrical object, such as a rotating shaft, the focusing lens may be a cylindrical lens with a focal length greater than the rotational radius of the cylindrical object around its axis of rotation. The cylindrical lens may collect reflected cylindrical wave from the surface of the object and convert it to a plane wave that interferes with the internal reference illumination plane waves.

Figure 4:
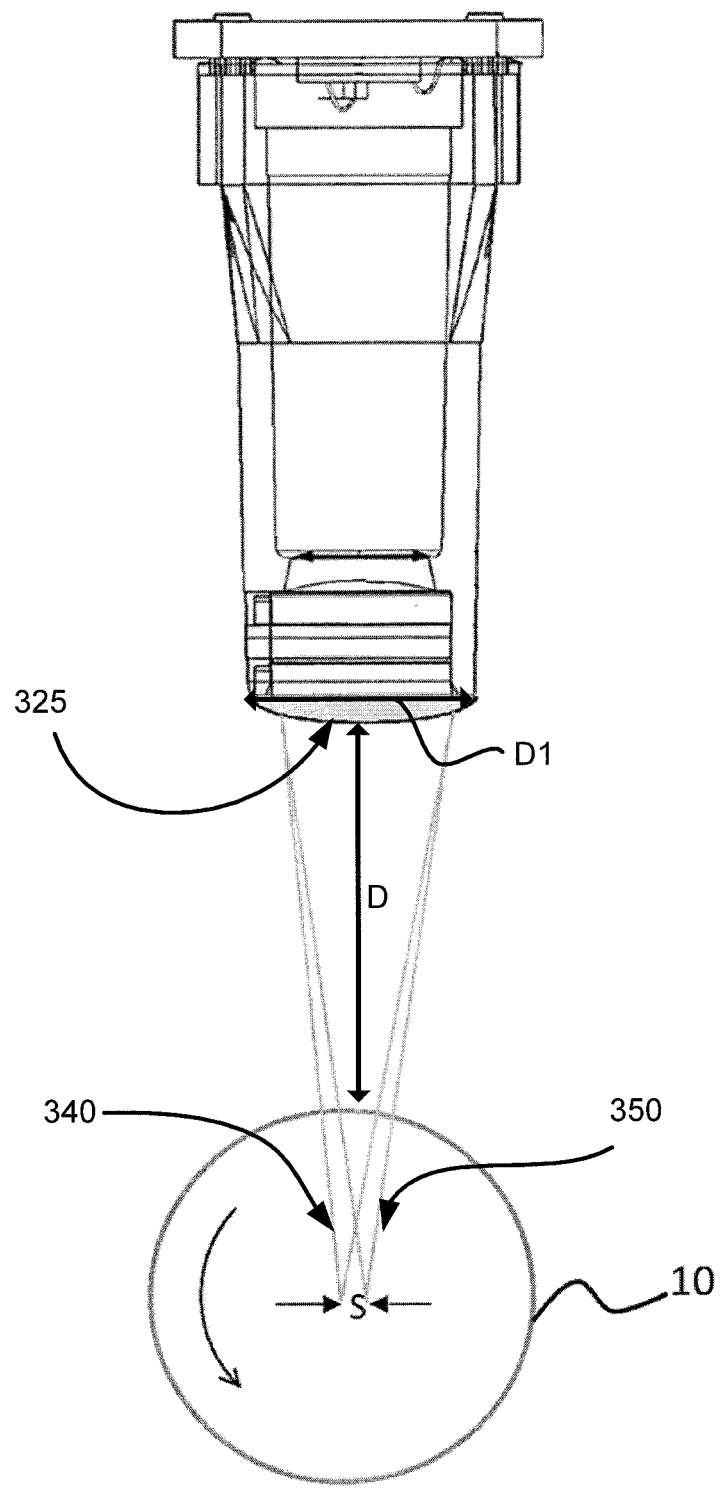
FIG. 4 is a schematic representation of another exemplary interferometer for measuring rotational movement, according to embodiments of the present disclosure.

FIG. 4 is a schematic representation of another exemplary interferometer for measuring rotational movement, according to embodiments of the present disclosure. The exemplary interferometer may be constructed based on the interferometer as shown in FIG. 3A of International Publication No. PCT/IB2017/000617. As shown in FIG. 4, a focusing lens 325 may replace the wedge shown in FIG. 3A of International Publication No. PCT/IB2017/000617 as the external element of the exemplary interferometer. When object 10 is a spherical object rotating around its center of rotation, focusing lens 325 may be a spherical or aspherical lens converging an illumination plane wave to a spherical wave focused at the center of rotation. When object 10 is a cylindrical object or any other object rotating around a single rotation axis, such as a shaft, focusing lens 325 may be a cylindrical lens converging the illumination plane wave to a cylindrical wave focused at the axis of rotation. In such instances, focusing lens 325 may also be a spherical or aspherical lens focused to the axis of rotation.

In some embodiments, as shown in FIG. 4, focusing lens 325 of the interferometer is at a working distance D away from the surface of object 10. An illumination beam 340 and a reflection beam 350 are spherical waves focused at two focal points the same distance away from focusing lens 325 and the center of rotation of object 10. The lateral offset between the two focal points is shown as S in FIG. 4. In some embodiments, illumination beam 340 is a spherical wave focusing at the center of rotation of object 10 and reflection beam 350 is spherical wave focusing at a focal point having a lateral offset S from the center of rotation of object 10. In other embodiments, reflection beam 350 is a spherical wave focusing at the center of rotation of object 10 and illumination beam 340 is spherical wave focusing at a focal point having a lateral offset S from the center of rotation of object 10. In yet other embodiments, both the illumination beam 340 and the reflection beam 350 are focused at a point laterally offset from the center of rotation of object 10, where the focusing points are offset from each other by a lateral offset S.

As described herein, the lateral offset S between the focal points of illumination beam 340 and reflection beam 350 is proportional to the angle between the reflection beam and illumination beam, such as the angle $\beta$ between the centerlines of the reflection beam and illumination beam as shown in FIG. 4. The overlap between illumination beam 340 and reflection beam 350 can be reduced as the working distance between the interferometer and the rotating object surface increases. It is contemplated that increasing the overlap between the illumination beam and reflection beam increases the signal to noise ratio (SNR) at a desired working distance D. Thus, various factors, such as measurement accuracy, focal length, the variation of distance, beam size, and sensors size, may be adjusted to maximize the SNR at the desired working distance D.

It is contemplated that reducing the ratio D/D1 may increase the overlap between the illumination beam and reflection beam and thus increase the SNR. In some embodiments, to maintain the overlap between illumination beam 340 and reflection beam 350, the working distance D may satisfy D<k*D1*δ/λ, where k is a factor smaller than 1 (e.g., 0.9), δ is the period of the diffraction grating of the interferometer, D1 is the diameter of focusing lens 325 or the diameter of illumination beam 340, and λ the wavelength of illumination beam 340. When k=0.85, δ=10 μm, and λ=0.85 μm, for example, D/D1 is smaller than about 10. The ratio D/D1 may become smaller when the grating period is smaller, or the wavelength of illumination beam 340 is greater. For example, a grating period may be 5 μm instead of 10 μm. Therefore, a smaller k, a smaller working distance D, and/or a larger diameter D1 of the focusing lens 325 may reduce the ratio D/D1 and allow for greater overlap between illumination beam 340 and reflection beam 350 and thus greater SNR.

In some embodiments, reducing the diameter D1 of focusing lens 325 may increase the SNR for measuring object 10, allowing for better accuracy for measuring the rotation of object 10. For example, when a focusing lens 325 having a smaller diameter D1 is used, intensity of illumination beam 340 on object 10 is increased. The SNR increases with the intensity because the intensity of illumination beam 340 is determined by the power of illumination beam 340 divided by the area of illumination on object 10. In some instances, the power of illumination beam 340 is limited by its application, such as for an eye tracking application where the power is limited for safety purposes, or by the power of available light sources, such as laser diodes. Thus, it is contemplated that for a given power of illumination beam 340, a smaller beam diameter increases the intensity of illumination beam 340 and the resulting SNR. However, because a motion tracking error is proportional to the ratio δ/D1, where δ is the motion tracking resolution unit, δ=λ/sin(θ), and λ is the wavelength of illumination beam 340, reducing D1 may increase the motion tracking error. Thus, D1 may be chosen by balancing the desired motion tracking accuracy and maximizing the SNR for a certain working distance D.

Consistent with the present disclosure, the offset S can be calculated by S=sin(β)*f, where f is the focal length of focusing lens 325 and β is the angle between illumination beam 340 and reflection beam 350 inside the sensor. The linear relationship between measured phase change and amount of rotation becomes dL(θ)/d θ≈R*k=S=f*sin(β). Thus, the rotational measurement may be independent of the radius or the shape of the rotating object. The object does not need to be spherical or cylindrical, and can have any irregular shape and radius of rotation.

In some instances, at least one of the focal points of illumination beam 340 and reflection beam 350 may be axially offset from the center of rotation of object 10. As a non-limiting example, one of the focal points of illumination beam 340 and reflection beam 350 may be axially closer to the light detector and further from the center of rotation of object 10 than desired. As another non-limiting example, one of the focal points of illumination beam 340 and reflection beam 350 may be axially too far away from the light detector and the center of rotation of object 10. Such large axial offsets of the focal points may degrade the linear relationship between the measured phase change and amount of rotation, resulting in a spread in the measured amount of rotation of an object that rotates at a constant angular speed, such as a spread in the measured angular frequency.

Consistent with embodiments of the present disclosure, the spread in the measurement described above may be used for implementing an autofocusing process to adjust the focal point of illumination beam 340 or reflection beam 350 to reduce the spread in the measured amount of rotation of object 10. For example, the interferometer may include a processor configured to determine an offset of the focal point from a center of rotation of object, and to trigger an autofocus process. A feedback signal for autofocusing may be determined based on the full width at half maximum (FWHM) of a smooth fit, such as a Gaussian fit, of the spectrum or distribution for a qualified rotational measurement. The inverse of the FWHM may be used as a merit function in an iterative algorithm for adjusting the focal point of illumination beam 340 or reflection beam 350 to achieve autofocusing of illumination beam 340 or reflection beam 350.

As described herein, various suitable methods may be used to adjust the focal point of illumination beam 340 or the focal point of reflection beam 350. For example, the sensor of the interferometer may be moved towards or away from object 10; focusing lens 325 may be moved towards or away from the sensor; focusing lens 325 may be a lens with adjustable focal length, such as a liquid lens or a stress induced lens. The control of the positioning of the sensor or focusing lens 325 may be made using various suitable methods. For example, a voice coil motor or a piezo motor may be used for positioning the sensor or focusing lens 325.

In some applications, a relatively large working distance from the interferometer to the object to be measured is desired, such as in eye tracking in VR or AR headsets. Thus, the interferometer consistent with the present disclosure may include a plurality of optical elements to allow for a desired working distance. For example, when a relatively large working distance is desired, more than one lens may be used for illuminating object 10 and for receiving the reflected illumination. In such instances, one or more lenses may have a focal point close to the center of rotation of the object.

Various configurations of the lenses of the interferometer may allow for obtaining approximately linear dependence between the overall phase change and the amount of rotation of object 10. For example, one or more focusing lenses may not focus the illumination beam to the center of rotation of object 10. One or more lenses for receiving the reflected illumination, i.e., the reflection beams, from object 10 may have a focal point at a distance away from the center of rotation of object 10 to compensate for the deviation of the illumination wave. For example, object 10 may be illuminated by a plane illumination wave and one or more lenses collecting the reflected illumination beam may be focused to a point about half of the radius of object 10 closer to the sensor than the rotational axis of object 10.

Figure 5D:
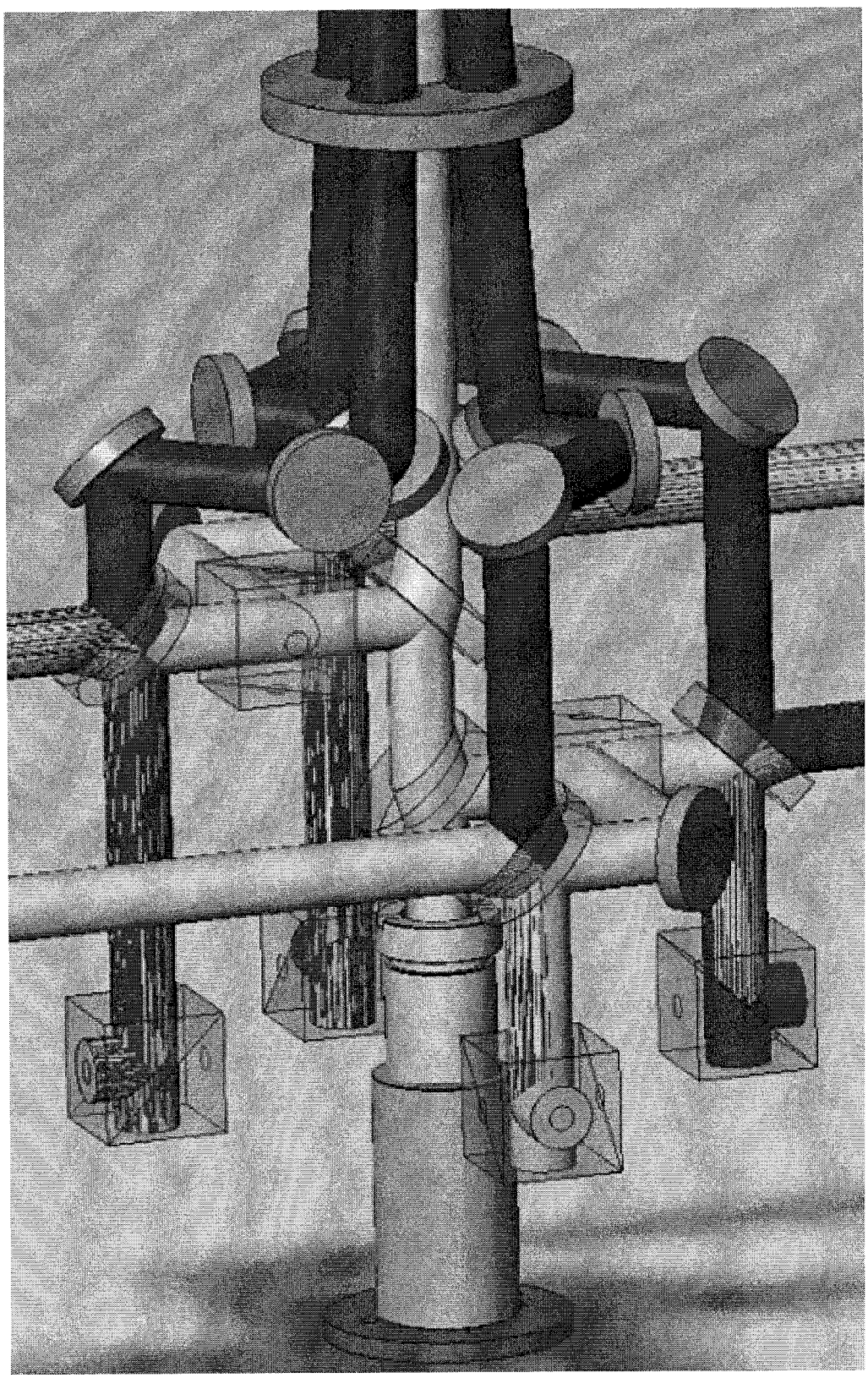
FIG. 5D is a diagrammatic representation of the outbound and inbound optical paths in a specific exemplary interferometer, according to embodiments of the present disclosure.

FIG. 5A is a schematic cross-sectional representation of an exemplary interferometer 100 for measuring rotational movement, according to embodiments of the present disclosure. FIG. 5B is a schematic horizontal cross-sectional representation of the exemplary interferometer of FIG. 5A. FIG. 5C is another schematic horizontal cross-sectional representation of the exemplary interferometer of FIG. 5A. FIG. 5D is a diagrammatic representation of the outbound and inbound optical paths in a specific exemplary interferometer 100. As shown in FIG. 5A, exemplary interferometer 100 may be positioned at a working distance D away from an object 10. For example, interferometer 100 may have a window 170 and object 10 may have a curved surface 101. In this example, working distance D may be the distance from window 170 to curved surface 101.

As described above, object 10 may have any shape. For example, object 10 may be a spherical object having a center of rotation O or a cylindrical object having a centerline. In one embodiment, object 10 may or may not have rotational symmetry. Object 10 may be configured to rotate about at least one rotational axis. Interferometer 100 is configured to measure the rotational movement of object 10 about the at least one rotational axis in accordance with embodiments of the present disclosure.

As shown in FIG. 5A, interferometer 100 may include a housing 105 and a light source 110 located within housing 105. Light source 110 may be a coherent light source, such as a laser, emitting an illumination beam. The illumination beam may be a coherent illumination beam. For example, light source 110 may be a VCSEL having a relatively long coherence length, such as a coherence length is greater than twice the working distance D In some embodiments, as shown in FIG. 5A, the illumination beam may expand out in a cone from light source 110. In other embodiments, the illumination beam may be collimated.

Interferometer 100 may include at least one optical element configured to modify the projected coherent illumination beam in a manner accounting for a rotation of object 10. In some embodiments, as shown in FIGS. 5A and 5C, interferometer 100 may include a focusing lens L1 that may modify the illumination beam by converging the illumination beam to the center of rotation O of object 10. In other embodiments, focusing lens L1 may modify the illumination beam by converging the illumination beam to a focal point at a small offset from the center of rotation O of object 10.

With reference to the disclosure of FIG. 4, D1 may refer to the diameter of focusing lens L1 or the diameter of the output illumination beam from focusing lens L1. The working distance D may be less than about 10 times of the diameter D1. Focusing lens L1 may be placed as close as possible to surface 101 of object 10 and as far as possible from light source 110. The working distance D and the diameter D1 of focusing lens L1 may be selected to be large enough to obtain a high SNR and satisfactory measurement accuracy but also small enough to allow for a compact design of interferometer 100.

In some embodiments, as shown in FIGS. 5A and 5C, interferometer 100 may include one or more collection lenses L2 for collecting reflections of the illumination beam, i.e., reflection beams, from surface 101 of object 10. As described herein, D2 may refer to the diameter of collection lens L2. As used herein, the angle θ may refer to the angle of a reflection beam from object 10 collected by collection lens L2. Angle θ may also refer to the angle between the centerlines of the illumination beam and the reflection beam. In some embodiments, as shown in FIG. 5C, interferometer 100 may include two or more collection lenses L2 to collect two or more reflection beams from surface 101 of object 10 in two or more different non-collinear collection directions.

As shown in FIG. 5A interferometer 100 may include at least one sensor 115 located within housing 105 and connectable to a processor 125 that may be located within housing 105 or outside housing 105. As shown in FIG. 5B, sensor 115 may include at least one light detector 120, such as a photodiode. In some embodiments, sensor 115 may include a plurality of light detectors 120. Each light detector 120 may detect a reflection beam from surface 101 of object 10 in a direction having a different angle of reflection. As a non-limiting example, when sensor 115 includes three light detectors 120, the detected interference signals by the three light detectors 120 are conveyed to processor 125. Thereafter, processor 125 may use the input from the sensor to determine an amount of rotation of object 10 around the at least one rotational axis. For example, determining the movement of object 10 in three dimensions, such as movement in three orthogonal dimensions of object 10 or rotational movement in two orthogonal dimensions and a translation movement of object 10.

In some embodiments, as shown in FIG. 5B, sensor 115 may include light detectors 120 in pairs, such as three or four pairs of light detectors 120. The use of pairs of light detectors 120 allows for the determination of the rotational direction of object 10 in a given dimension and/or the direction of translational movement of object 10. For example, each pair of light detectors 120 may detect polarized light in two orthogonal directions. Interferometer 100 may further include a first beam splitter 140 placed before each pair of light detectors 120. Beam splitter 140 may be a polarizing beam splitter or a non-polarizing beam splitter, such as a sinusoidal grating. When beam splitter 140 is a polarizing beam splitter, its axis is such that one polarization is transmitted toward one of the pair of light detectors 120 and the orthogonal polarization is transmitted to the other of the pair of light detectors 120. If the internal reference beam is linearly polarized at 45 degrees such that the polarizing beam splitter splits its power substantially evenly to both detectors, and the collected beam from the object is circularly polarized by circular polarizer 160, the interference signals detected by the pair of light detectors 120 will have a phase difference of 90 degrees. The sign of the phase difference can be used to determine the movement direction along a given dimension.

In some embodiments, light source 110 may emit linearly polarized illumination beam. Interferometer 100 may further include a circular polarizer 160 placed in the path of the radiation from surface 101 of object 10. The use of the circular polarizer 160 allows for enforcement of a specific polarization on the reflection beam from surface 101 of object 10.

As shown in FIG. 5A, interferometer 100 may further include a second beam splitter 130. Beam splitter 130 may be a diffraction grating. Beam splitter 130 may split the illumination beam into a plurality of internal reference beams each of which has a different direction. In some embodiments, an internal reference beam may be reflected by beam splitter 130 towards sensor 115. In other embodiments, an internal reference beam may be directed to sensor 115 by one or more optical elements. For example, as shown in FIG. 5A, an exemplary internal reference beam may be diffracted in reflection from beam splitter 130 towards a mirror 180. Mirror 180 may be tilted for adjusting the direction of the internal reference beam. Mirror 180 may have a flat reflecting surface or may be curved to reduce the expansion of the internal reference beam.

In some embodiments, as shown in FIG. 5A, interferometer 100 may further include a lens 190. Lens 190 may be used with mirror 180 to adjust the angle of an internal reference beam to match the angle of a reflection beam from object 10 collected by lens L2. For example, an internal reference beam reflected from mirror 180 may be directed to lens 190. Lens 190 may be used with an optional lens on mirror 180 to make the internal reference beam collimated when it gets to a partially reflecting surface 150. Lens 190 may also be used with lens L2 to make the collimated internal reference beam have an angle θ that matches the angle of a reflection beam from object 10.

In some embodiments, partially reflecting surface 150 may have a tilt to align the internal reference beam reflected from partially reflecting surface 150 to the reflection beam transmitted through partially reflecting surface 150 in the same direction. The tilt may be created by a wedge with respect to partially reflecting surface 150. For example, when beam splitter 130 is a diffraction grating outputting an internal reference beam having a diffracted angle of 15° and mirror 180 has flat surface, a wedge having a suitable angle at partially reflecting surface 150 may be selected to change the direction of the internal reference beam from 15° to θ to match the angle of a reflection beam from object 10.

As described herein, beam splitter 130 may split an illumination beam from light source 110 into a plurality of internal reference beams to interfere with a plurality of reflection beams. Interference signals resulting from the interference of the internal reference beams and the reflection beams are collected by a corresponding number of collection lenses L2 and then detected by a corresponding number of light detectors 120. Each of the resulting interference signals is linearly proportional to the amount of movement, such as the amount of rotation, of object 10 in a given dimension.

One or more of the optical elements described above may be used to align each internal reference beam with a corresponding reflection beam from object 10. In the exemplary interferometer example depicted in FIG. 5D the outbound and inbound optical paths are illustrated. Specifically, beam splitter 130 may split the illumination beam into four internal reference beams having four different directions. In such instances, interferometer 100 may include four collection lenses L2, four light detectors 120 or four pairs of light detectors 120, four mirrors 180, four lenses 190, and/or four partially reflective surfaces 150 to change the direction of each of the internal reference beam. Each internal reference beam reflected by partially reflecting surface 150 may propagate towards light detector 120 along the same direction as a corresponding reflection beam transmitting through partially reflecting surface 150. Each internal reference beam may further interfere with the corresponding reflection beam, generating an interference signal linearly related to the amount of rotation of object 10 in a certain dimension.

Figure 6:
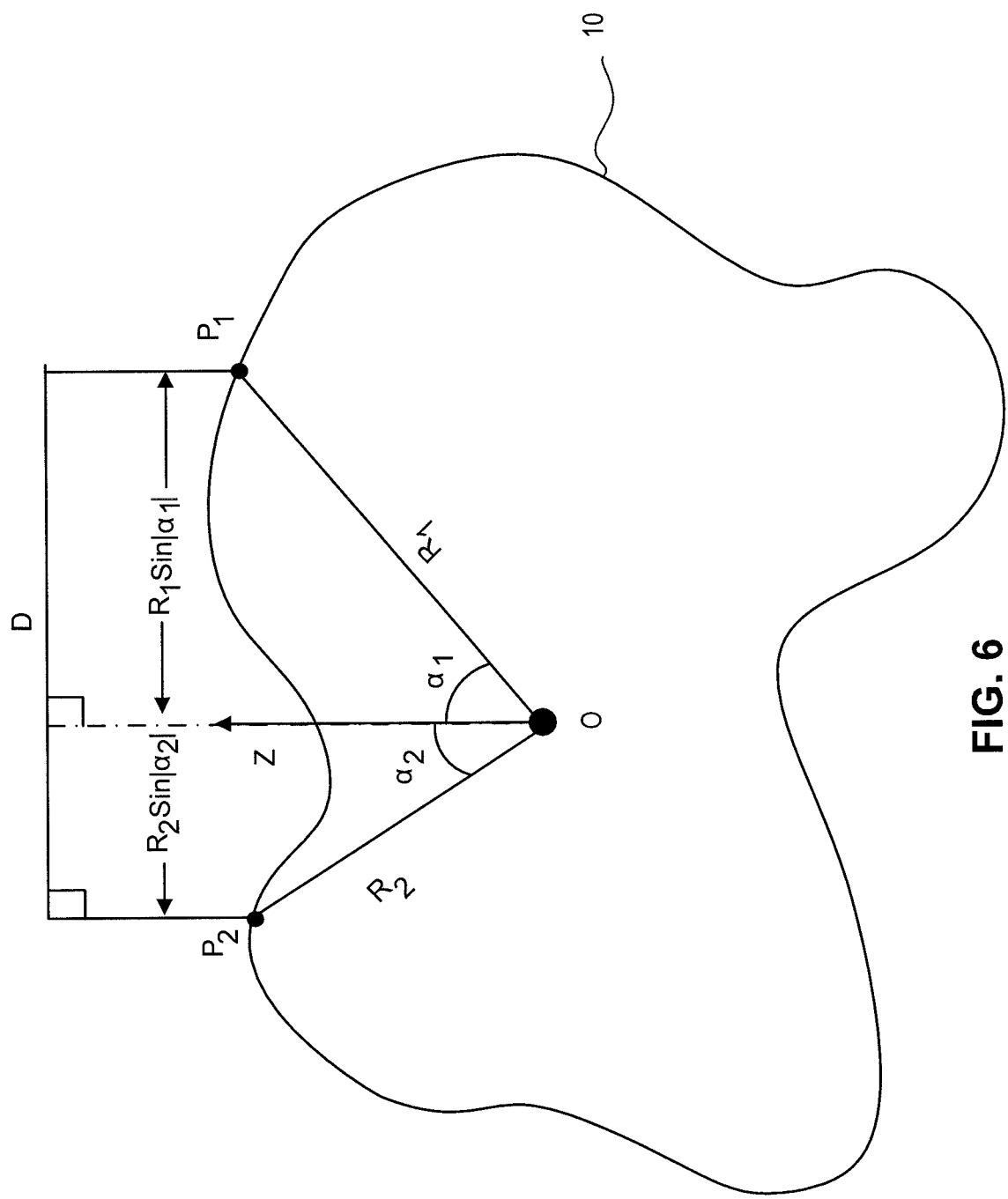
FIG. 6 graphically illustrates another exemplary optical model for measuring rotational movement, according to embodiments of the present disclosure.

The following with reference to FIGS. 6 and 7 describes an exemplary interferometer for measuring rotational movement of an object of any shape using one or more parallel illumination beams consistent with the present disclosure.

Consistent with embodiments of the present disclosure, the interferometer may use more than one illumination beams for measuring the rotation of an object of any shape. The at least one optical element of the interferometer may include a beam splitter, such as a diffraction grating configured to split the projected coherent light into at least two beams, such as three or four beams, configured to travel parallel towards different areas of the object. For example, the beam splitter may modify the projected coherent light by splitting the projected coherent light into at least two parallel beams for concurrently illuminating different areas of the rotating object. The beam splitter may be a two-dimensional diffraction grating splitting the projected coherent light into at least two parallel beams, such as four parallel beams.

FIG. 6 graphically illustrates another exemplary optical model for measuring rotational movement, according to embodiments of the present disclosure. As shown in FIG. 6, an object 10 having a non-symmetric irregular shape has a center of rotation O. $P_1$ and $P_2$ are two arbitrary points on the surface of object 10. As shown in FIG. 6, $\alpha_1$ is the angle of the line $OP_1$ to the Z axis, and $\alpha_2$ is the angle of the line $OP_2$ to the Z axis. As described herein, a positive angle corresponds to an angle of a line tilted clockwise from the direction Z. Thus, $\alpha_1$ may be a positive angle and $\alpha_2$ may be a negative angle. Assuming dθ is the instantaneous rotational angle of object 10, the Z component of the movement of point $P_1$ is $R_1*\sin(\alpha_1)*d\theta$, and the Z component of the movement of $P_2$ is $R_2*\sin(\alpha_2)*d\theta$. Subtracting these two values from each other gives $(R_1*\sin(\alpha_1)-R_2*\sin(\alpha_2))*d\theta = (R_1*\sin(\alpha_1)+R_2*\sin(|\alpha_2|))*d\theta = D*d\theta$, where D is the distance between $P_1$ and $P_2$ in the direction perpendicular to Z. Therefore, if the movement in the Z direction of two points on the surface of object 10 that are separated for a known distance D in the direction perpendicular to the Z direction can be measured, the rotational angle dθ of object 10 can be obtained.

The movement in the Z direction of two points on the surface of object 10 can be measured by illuminating object 10 using two parallel illumination beams and collecting the reflections of the illumination beams in the same direction. Such configuration allows measuring the movement of two points along the illumination wave fronts, which is the Z direction. The measured movement in the Z direction does not depend on the shape, radius, rotational radius, or center of rotation of object 10. Thus, object 10 may have any shape. Object 10 may have or may not have rotational symmetry.

Figure 7A:
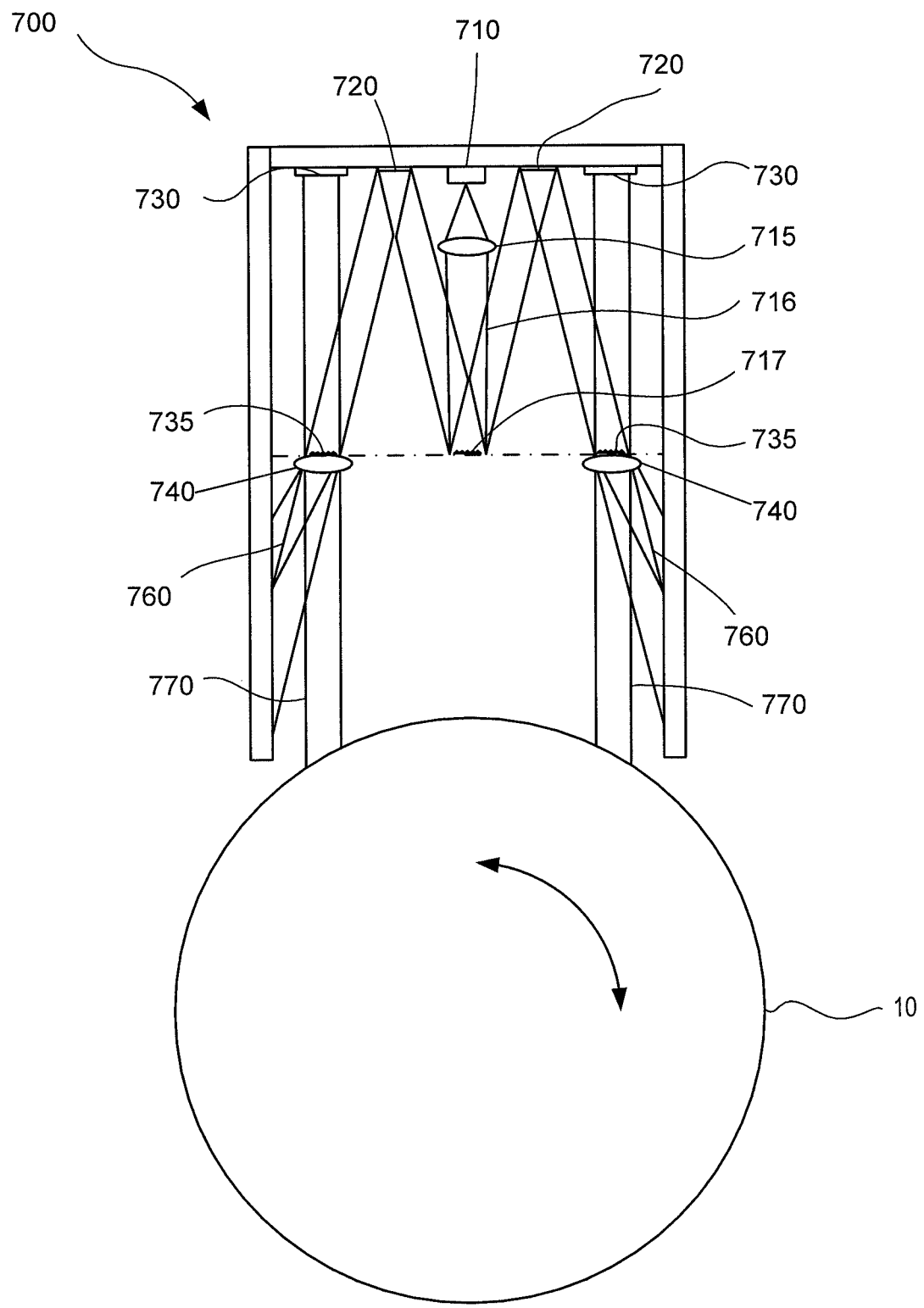
FIG. 7A is a schematic representation of another exemplary interferometer for measuring rotational movement, according to embodiments of the present disclosure.

FIG. 7A is a schematic representation of an exemplary interferometer 700 for measuring rotational movement based on the optical model of FIG. 6, according to embodiments of the present disclosure. As described above, object 10 may be of any shape. Interferometer 700 may be used for measuring the amount of rotation of object 10 without prior knowledge the shape or radius of object 10.

Consistent with embodiments of the present disclosure, as shown in FIG. 7A, interferometer 700 may include a light source 710 and one or more light detectors 730. As described herein, interferometer 700 may include more than one light source 710 and a corresponding number of lenses 715 to generate two or more illumination beams. Interferometer 700 may include one or more optical elements that modify an illumination beam 716 from light source 710 in a manner accounting for a rotation of object 10.

In some embodiments, an illumination beam emitted by light source 710 may be collimated by a lens 715 and directed towards a grating 717. Grating 717 may be a reflective diffraction grating. For example, as shown in FIG. 7A, a collimated illumination beam 716 may be diffracted and reflected by diffraction grating 717 and split into two separate illumination beams in different directions. The directions or angle of reflection of the diffracted illumination beams may be determined by the wavelength of the illumination beam and the pitch of diffraction grating 717. For example, the wavelength of light emitted by light source 710 may be 850 nm. The pitch of diffraction grating 717 may be about 10 μm. In some embodiments, when measurement of rotation of object 10 in two dimensions is desired, diffraction grating 717 may be a two-dimensional grating allowing for splitting illumination beam 716 into four separate beams.

As shown in FIG. 7A, interferometer 700 may further include one or more mirrors 720 and one or more diffraction gratings 735. Illumination beams generated by diffraction grating 717 can be separately reflected by mirrors 720 towards diffraction gratings 735. In some embodiments, diffraction gratings 735 may have the same pitch as diffraction grating 717. Diffraction gratings 735 may split each of the illumination beam reflected by mirror 720 into one or more output beams. For example, as shown in FIG. 7A, each diffraction grating 735 may split the illumination beam into three forward-diffracted beams 760, including one forward-diffracted beam 770 directed towards object 10. The other forward-diffracted beams may be blocked and/or absorbed by the housing of interferometer 700. As shown in FIG. 7A, the forward-diffracted beams 770 generated by diffraction grating 735 may both illuminate object 10 and be parallel to each other.

Diffraction gratings 735 may be designed to back-diffract some of the illumination beam it received towards detectors 730. Diffraction gratings 735 may generate one or more back-diffracted beams. At least one of the back-diffracted illumination beams may be reflected towards detector 730 and used as an internal reference beam that interferes with reflections of an illumination beam from object 10 to generate an interference signal for determining the rotational movement of object 10. For example, as shown in FIG. 7A, reflections of two forward-diffracted illumination beams 770 from rotating object 10 may be directed towards detectors 730 and interfere with the back-diffracted illumination beams to generate the interference signals indicative of the amount of rotation of object 10. Back-diffracted illumination beams by diffraction grating 735 not directed towards detector 730 may be blocked and/or absorbed by the housing of interferometer 700.

In some embodiments, interferometer 700 may include a suitable number of the optical elements described above to generate multiple parallel illumination beams 770. The multiple parallel illumination beams 770 may illuminate different points on the surface of object 10 having different distances D between each two points to increase the measurement accuracy. For example, each two of the multiple parallel illumination beams 770 may be used to determine the amount of rotation of object 10 in a given dimension. Using multiple illumination beams 770 that are not on the same plane also allows for measuring rotational movement of object 10 in two dimensions.

Interferometer 700 may include lenses 740 adjacent to diffraction gratings 735 to focus the parallel illumination beams 770 to focal points at the same plane with the center of rotation O of object 10. In some embodiments, lenses 740 may focus one of the parallel illumination beams 770 to the center of rotation of object 10 and focus the other parallel illumination beams 770 to focal points laterally offset from the center of rotation of object 10. In other embodiments, lenses 740 may focus all of the parallel illumination beams 770 to focal points that are laterally offset from the center of rotation of object 10. For example, when two parallel illumination beams 770 are used, one of the two parallel illumination beams 770 may be focused to the center of rotation O of object 10 while the other may be focused to a point laterally offset from the center of rotation O of object 10. The reflection beams (not shown) may follow the same optical paths of the parallel illumination beams 770 and similarly focused as the parallel illumination beams 770. The focused illumination and reflection beams may further improve the SNR of interferometer 700 by causing the phase relations of the different reflectors across the surface of object 10 to change more linearly with the rotation of object 10 than for non-focused beams. This is also illustrated by the exemplary interferometer described below with reference to FIGS. 7B and 7C.

Figure 7B:
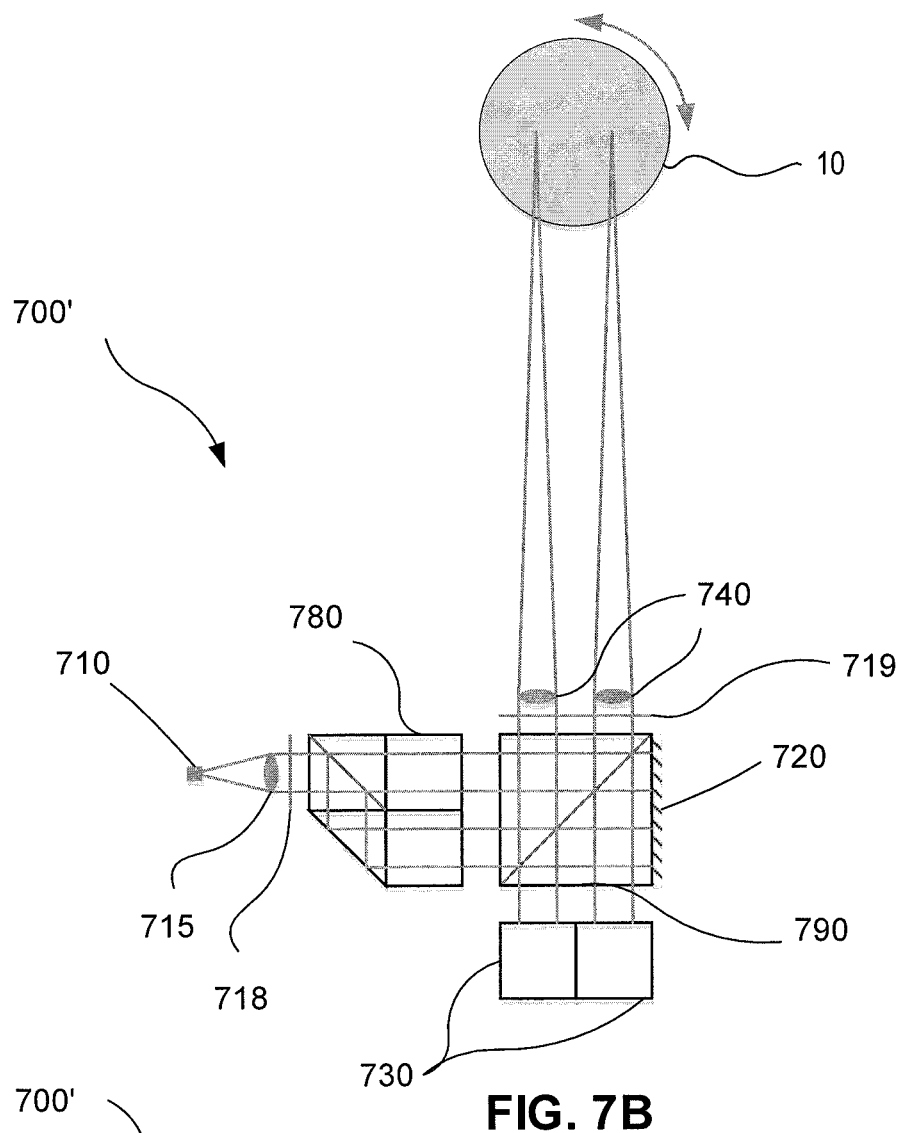
FIG. 7B is a schematic representation of another exemplary interferometer for measuring rotational movement, according to embodiments of the present disclosure.
Figure 7C:
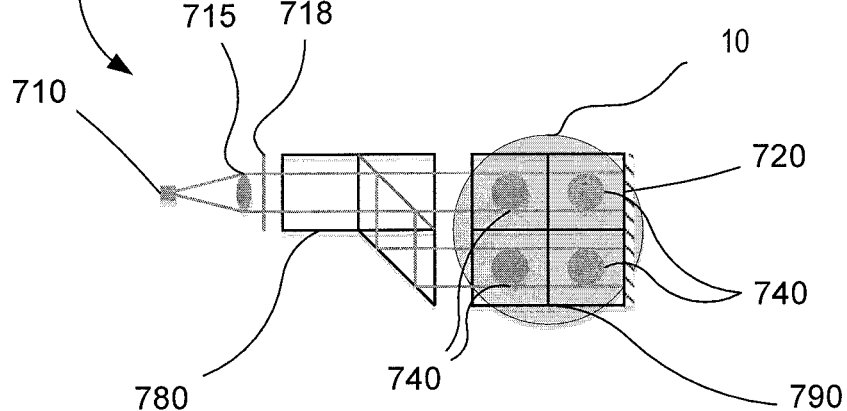
FIG. 7C is a schematic horizontal cross-sectional representation of the exemplary interferometer of FIG. 7B.

FIG. 7B is a schematic representation of another exemplary interferometer 700' for measuring rotational movement, according to embodiments of the present disclosure. FIG. 7C is a schematic horizontal cross-sectional representation of the exemplary interferometer 700' of FIG. 7B. As shown in FIGS. 7B and 7C, interferometer 700' allows for focusing multiple parallel illumination beams 770 arranged in two dimensions to focal points offset from the center of rotation O of object 10 for the same distance for measuring rotational movement of object 10 in two dimensions with higher SNR.

As shown in FIGS. 7B and 7C, in some embodiments, interferometer 700' includes a light source 710. Light source 710 may emit an expanding illumination beam, which may be collimated by lens 715. Interferometer 700' may further include a beam doubler 780 and a beam splitter 790. Beam doubler 780 includes a combination of beam splitters that split the collimated illumination beam from lens 715 into multiple parallel beams distributed in two dimensions. For example, as shown in FIGS. 7B and 7C, beam doubler 780 splits a collimated illumination beam from lens 715 into four parallel illumination beams arranged in two dimensions. Each of the four parallel illumination beams is partially directed towards object 10 by beam splitter 790 and partially transmits through beam splitter 790. The transmitted illumination beams serve as internal reference beams and are reflected by mirror 720 and then directed to detectors 730 by beam splitter 790. Lenses 740 focus the four parallel illumination beams to four focal points preferably at the same plane as the center of rotation of object 10. The two-dimensional arrangement of the parallel illumination beams allows for measuring rotational movement of object 10 around two independent rotational axes, and also measure the linear movement of object 10 towards and away from interferometer 700.

In some embodiments, interferometer 700' may include a circular polarizer 718 after lens 715 and a linear polarizer 719 before lens 740. The use of these polarizers together with polarization detectors 730 allows for determining the movement direction of object 10 along a given dimension as described above with reference to FIG. 5A.

As described herein, other configurations of the interferometer for measuring rotational movement are possible using additional optical elements, such as mirrors, lenses, etc., consistent with the present disclosure. The interferometer may have any suitable configuration consistent with the exemplary optical models and design principles described above. For example, embodiments of the interferometer consistent with the present disclosure may be constructed using off-the-shelf components, such as commercially available light sources, beam splitters, mirrors, lenses, polarizers, light detectors etc. The path of the optical beams in the interferometer may be adjusted based on the chosen optical components consistent with the present disclosure to obtain interference signals containing information of the amount of movement of an object. Using off-the-shelf components may advantageously allow for mass production of inexpensive optical tracking devices suitable for various applications, such as eye tracking in AR and VR applications further described below.

In some embodiments, the interferometer may be installed in a display device, such as a head-mounted display device or a television set. For example, when used for eye tracking, the interferometer may be installed in or connected to eyeglasses with a beam of the interferometer arranged to impinge on an eyeball and to track the gaze of the eyeglass wearer by measuring rotation of the eyeball. By way of example, the interferometer may be installed in or connected to the eyeglass frame, bridge, rim, hinge, end piece, lens pad arm, or temple. Depending on location, one or more mirrors may or may not be used to direct the beam toward to the eyeball. By way of another no limiting example, the interferometer may be incorporated into an AR or VR headset.

The device may include a memory configured to store a resting position of the eye and at least one processor. The at least one processor may be configured to display content to the user; determine an amount of rotation of the eye around the at least one rotational axis based on a relative phase difference between the detected reflections and internal reference beams, identify a position of the eye relative to the resting position; and change the content displayed to the user in response to the identified position of the eye of the user.

Eye Tracking Using an Interferometer Consistent with the Present Disclosure

Embodiments of the interferometer consistent with the present disclosure may be used to measure the movement of an eye. For example, the interferometer may be incorporated in a display device having at least one processor configured to track movements of the eye based on the interference signals received by the sensor. In some embodiments, the interferometer may be used for generating input, such as position of the eye relative to a resting position, for controlling the display device, such as a VR headset, an AR headset, or any content display device. For example, the display device may further include a memory configured to store a resting position of the eye and at least one processor. The at least one processor may be configured to display content to the user, determine an amount of rotation of the eye around the at least one rotational axis based on a relative phase difference between the detected reflections and internal reference beams, identify a position of the eye relative to the resting position, and change the content displayed to the user in response to the identified position of the eye of the user watching the display device. As described herein, the term "reference position" includes at least one of a reference direction and a reference location, or both.

In some embodiments, the interferometer may further include a computer-readable medium configured to store instructions or operational steps for performing signal processing algorithms for detecting characteristics of specific eye movements, such as fixation eye movement, saccadic eye movement, smooth pursuit movement, and blinks as described below.

Fixation eye movement is the movement of the eye when a person's eyes focus on a stationary target. When fixating on a stationary target, the eyes constantly move, both slowly lasting over about hundreds of milliseconds and fast lasting less than about ten milliseconds. Fixation eye movement typically has a small amplitude, for example, less than 1°. Since a typical eyeball is about 24 mm in diameter, a rotation of 1° corresponds to about 200 □m movement of the sclera. Therefore, for accurate tracking of the fixation eye movement, a detection resolution smaller than 20 □m is preferred.

Figure 8:
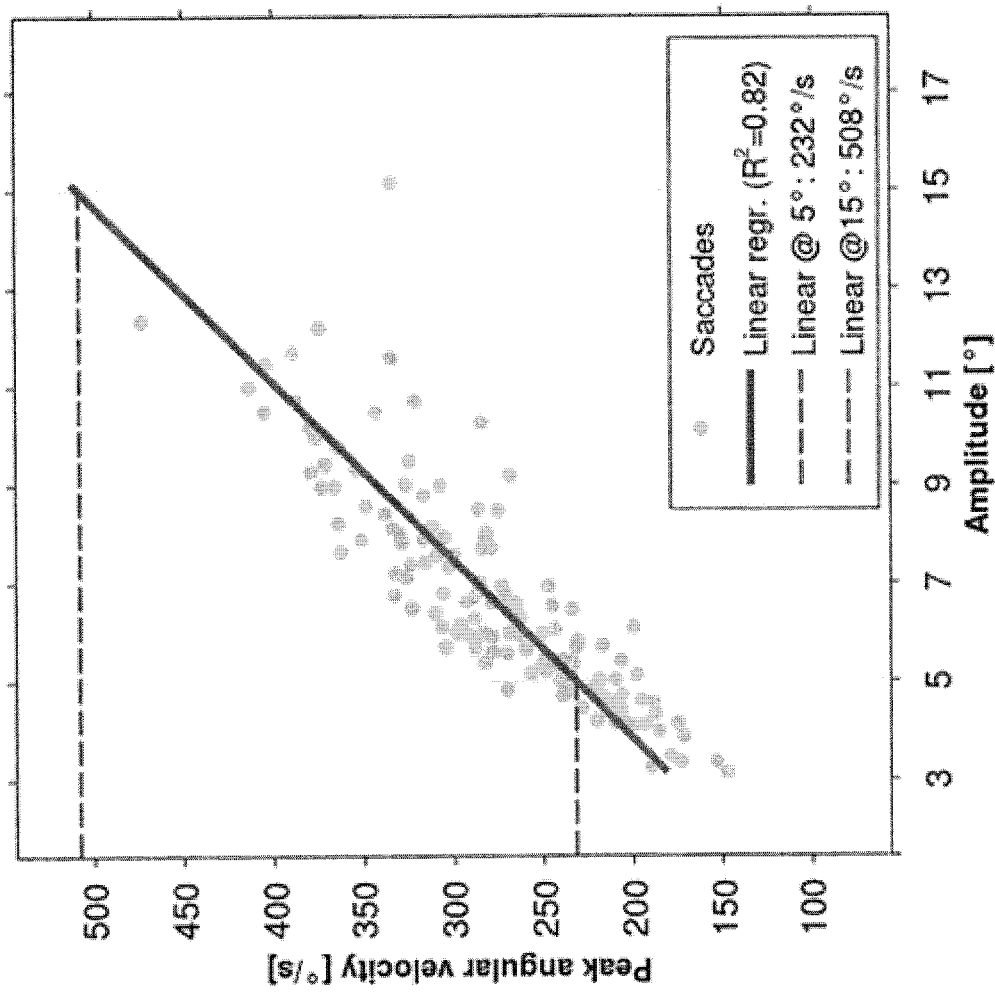
FIG. 8 graphically illustrates dependence of the peak angular velocity of saccadic eye movement on the amplitude of the movement.

Saccadic eye movement is a rapid jerk-like movement of the eyeball that serves to change the point of fixation of the eye. Saccadic eye movement range in amplitude from the small movements made while reading, for example, to the much larger movements made while gazing around a room. FIG. 8 graphically illustrates dependence of the peak angular velocity of saccadic eye movement on the amplitude of the movement. As shown in FIG. 8, the amplitude of saccadic eye movement is typically larger than 1° and the peak angular velocity of movement is typically linearly dependent on the amplitude of the movement. Saccadic eye movement lasts for about 20 or 30 milliseconds. The high peak velocities of saccadic eye movements result in linear velocities greater than 100 mm/sec. For example, a human eye may rotate at a peak angular velocity of about 232°/sec for a saccadic eye movement of about 5°, and a peak angular velocity of about over 500°/sec for a saccadic eye movement of about 15°. Accurate tracking of these fast movements requires a tracking time resolution of about 1 millisecond.

Smooth pursuit movement is the movement of the eyes while tracking a target's movement, so that its moving image can remain maintained on the fovea—the central area of the retina. The angular velocity of the eye during smooth pursuit movement depends on the target angular velocity. The angular velocity of the eye during smooth pursuit movement is typically smaller than that during saccadic eye movement.

Blinks are movements of the eye lids that momentarily cover the eyes. The peak velocity of the eye lid movement may be larger than about 100 mm/sec. The duration of a blink typically lasts for about a few hundred milliseconds.

Embodiments of the interferometer consistent with the present disclosure may have a response time on the order of milliseconds, allowing for accurate and fast tracking of movement of the eye, such as fixation eye movement, saccadic eye movement, and smooth pursuit movement. Additionally, embodiments of the interferometer consistent with the present disclosure may allow for a relatively large working distance and suitable illumination beam size for eye tracking. For example, at least one optical element is configured to be located between about 25 mm and about 50 mm from the eye of the user. The diameter of the output illumination beam may range from about 1 mm to about 5 mm. The light source of the interferometer may be selected to have a power and a wavelength within the safety limit for illuminating the eye. For example, the light source may be a laser configured to emit an illumination beam having a wavelength between about 850 nm and a power of less than about 0.78 milliwatt.

The following describes an exemplary use of interferometer 100 in a head-mounted display device (e.g., an AR or VR headset) for tracking eye movement at a relatively large working distance. In this non-limiting example, working distance D is about 30 mm, the illumination beam diameter or the diameter of focusing lens D1 is about 2 mm, the angle θ of the reflection beam from object 10 collected by collection lens L2 is about 4°, the pitch or period A of diffraction grating (e.g., beam splitter 130) may be about 3.4 µm, and the wavelength λ of light source is about 850 nm. Thus, the first order reflection angle of the internal reference beam can be calculated to be about 15° based on the relationship $\sin(\theta)=\lambda/\Lambda=\frac{1}{4}$. A suitable mirror 180 with or without a lens or a wedge on partially reflecting surface 150 is selected to correct the angle of the internal reference beam to 4° when directed towards partially reflecting surface 150 to align with the reflection beam from object 10. The resulting resolution of movement tracking can be calculated as $\delta=\lambda/\sin(\theta)$, which is about 12 □m.

In some embodiments, interferometer 100 is configured to have an imaging capability to increase the accuracy for tracking eye movement by providing the ability to identify "stationary" or reference positions on surface 101 of object 10. As shown in FIGS. 5B and 5C, interferometer 100 may include one or more pairs of imaging sensors 102 and imaging lenses L3. Imaging lenses L3 are arranged to image an area of surface 101 of object 10 onto the corresponding imaging sensors 102.

As a non-limiting example, in an eye-tracking application, blood vessels in the sclera can be imaged by interferometer 100. Light source 110 may be selected to emit an infrared illumination beam. The infrared illumination beam may enhance the visibility of blood vessels in the sclera. Different areas of the sclera may be imaged periodically on imaging sensors 102 to determine the return of the eye to its "resting" position and the offset of the eye from the "resting" position. Such information of the position of the eye allows for correcting for errors accumulated during eye tracking by interferometer 100.

In some embodiments, when more than one pair of imaging sensor 102 and imaging lens L3 are used, imaging sensors 102 and imaging lenses L3 may be arranged such that the imaged areas of surface 101 by the different imaging sensors 102 at least partially overlap. For example, the centers of lenses L3 may be offset from the centers of imaging sensors 102. This allows imaging sensor 102 to image a larger area of the sclera or iris. In some embodiments, imaging sensors 102 may be arranged to be able to image all of the sclera and/or iris. The ability to image a large area of the sclera and/or iris improves the quality of the correlation between images taken by imaging sensors 102 to images of the eye at "nominal" resting position. In other embodiments, 2D images of partially overlapping areas of the sclera may be taken by imaging sensors 102 and used to reconstruct a 3D image of the sclera. The constructed 3D image of the sclera may be used to improve the accuracy for eye tracking.

In some embodiments, imaging sensor 102 may include baffles to block scattered and stray light from being incident on imaging sensors 102. The baffles may also prevent light passing through optical elements not associated with imaging sensor 102. In some embodiments, interferometer 100 may further include optical filters placed before imaging sensors 102 and/or adjacent imaging lenses L3 to block or suppress strong illumination from light source 110 that may affect image collection. For example, a long pass or short pass filter designed to block the wavelength of light source 110 may be selectively used such that the light from light source 110 does not affect the quality of the images taken by imaging sensors 102.

Figure 9:
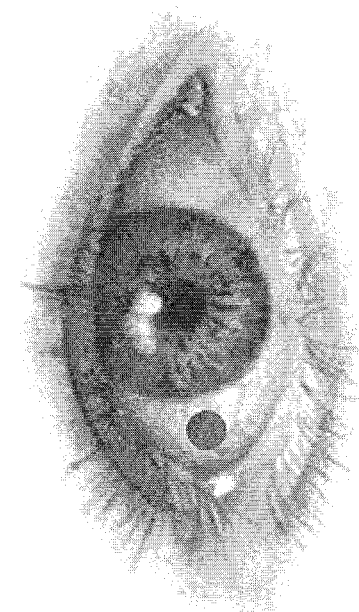
FIG. 9 graphically illustrates the location of the output illumination beam of an exemplary interferometer on a human eye, according to embodiments of the present disclosure.

In some embodiments, the output illumination beam of the interferometer may be directed to a location that is on a sclera of the eye closer to a corner of the eye than to a center of an iris of the eye, as shown by the circle in FIG. 9 to track various movements of the eye. Such location allows output illumination beam to seldomly reach the pupil. In some embodiments, the diameter of the output illumination beam is selectively to be smaller than about 2 mm, allowing for continuous tracking of eye movement while avoiding eye lashes. In addition, the images taken by imaging sensors 102 may be used to determine the location of the output illumination beam on the eye and assist in directing the output illumination beam to the desired location.

It is contemplated that when tracking eye movement, it may be desirable to turn off the light source when the illumination beam enters the pupil. As a non-limiting example, two interferometers may be used for illuminating different locations on the eye, such as at two locations on two sides of the pupil or corona. When one of the illumination beams of the two interferometers is about to enter the pupil, the corresponding light source is turned off while the other interferometer continues its measurement. As another non-limiting example, a plurality of interferometers may be used for measuring both eyes. For example, two interferometers may be used to separately measure the movement of two eyes. When the pupil of one of the eyes is about to be illuminated by one of the interferometers, the light source of that interferometers is turned off, but the other interferometer continues the measurement. Since movement of one eye is generally correlated with that of the other, measurement of the movement of one eye may provide at least partial information on the movement of the other eye.

It is contemplated that reflections of the illumination beam from surface 101 of object 10 may return into light source 110 and cause the power of light source 110 to oscillate due to interference of the reflected illumination beam and the internal reference beams. This phenomenon may result in an interfering signal that affects the measurement accuracy. In some embodiments, interferometer 100 may include a separate photodiode (not shown) configured to measure the power of the illumination beam from light source 110. Such separate photodiode may be placed adjacent to mirror 180 in the optical setup as shown in FIG. 5A. For example, one or more optical elements may be used to divert a small portion of the illumination beam to the separate photodiode. The signal detected by this separate photodiode is not responsive to the movement of object 10 and can be scaled and subtracted from the interference signals containing movement information, thereby reducing the interference caused by the reflections of the illumination beam returned to light source 110. Various signal processing techniques may be used to reduce the effects of this phenomenon as described in detail in International Publication No. PCT/IB2017/000617.

Figure 10:
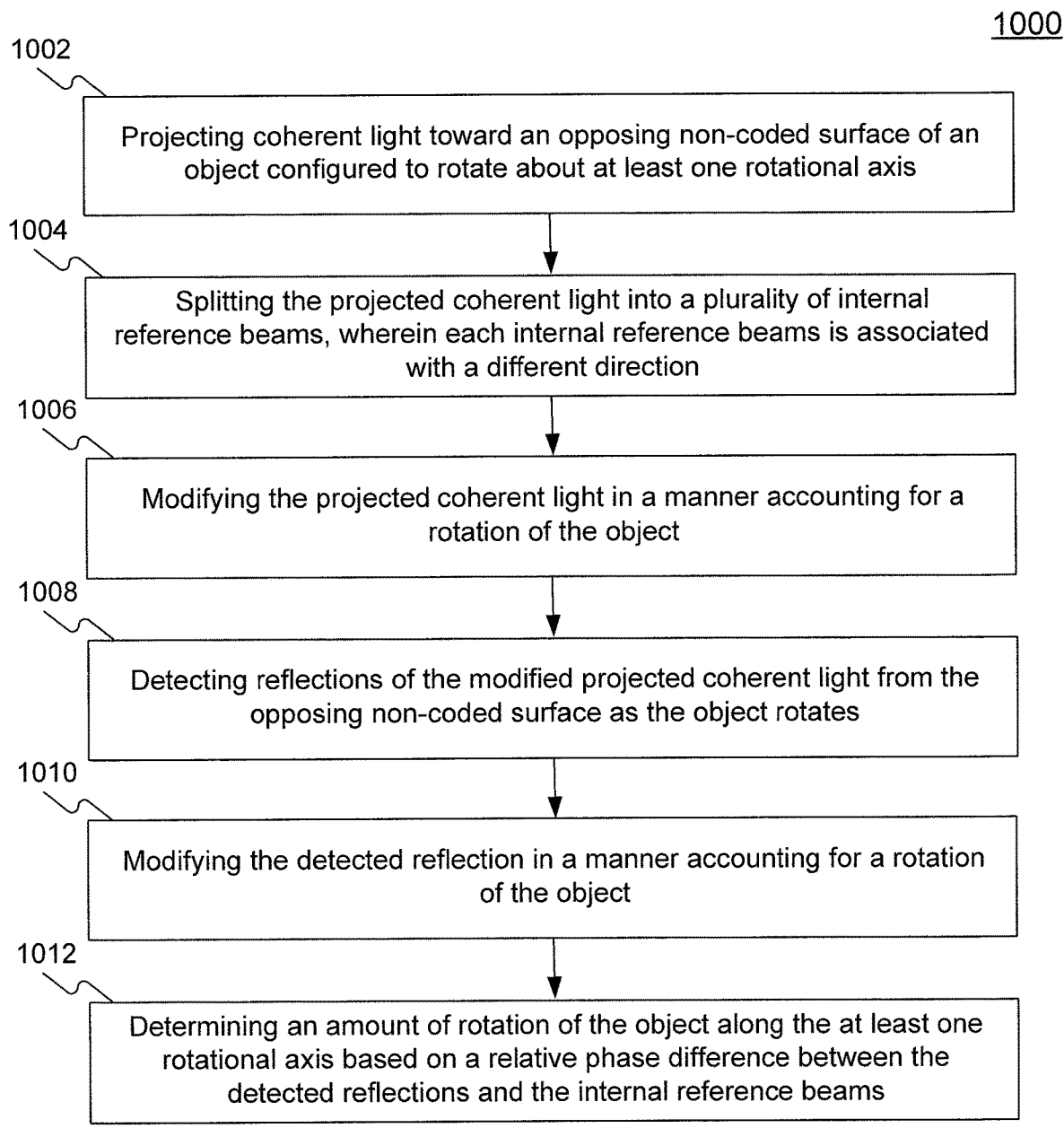
FIG. 10 is a flowchart of an exemplary method for measuring rotational movement, according to embodiments of the present disclosure.

Reference is now made to FIG. 10, which depicts an exemplary method 1000 for measuring rotational movement, consistent with the present disclosure. In one embodiment, all of the steps of method 1000 may be performed by interferometer 100. In the following description, reference is made to certain components of interferometer 100 for purposes of illustration. It will be appreciated, however, that other implementations are possible and that other components may be utilized to implement the exemplary method. It will be readily appreciated that the illustrated method can be altered to modify the order of steps, delete steps, or further include additional steps.

At step 1002, a light source (e.g., light source 110) may project coherent light toward an opposing non-coded surface of an object configured to rotate around at least one rotational axis. At step 1004, a beam splitter (e.g., beam splitter 140) may split the projected coherent light into a plurality of internal reference beams, wherein each internal reference beams is associated with a different direction. At step 1006, at least one optical element (e.g., focusing lens L1) may modify the projected coherent light in a manner accounting for a rotation of the object. In one example, when the object is a spheroid modifying the projected coherent light includes forming a spherical illumination wave converging to the center of rotation of the spheroid. In another example, when the object is a cylindroid modifying the projected coherent light includes forming a cylindrical illumination wave converging to an axis of rotation of the cylindroid. In another example, modifying the projected coherent light includes splitting the projected coherent light into the at least two beams for concurrently illuminating different areas of the object. At step 1008, a sensor (e.g., sensor 115) may detect reflections of the modified projected coherent light from the opposing non-coded surface as the object rotates. At step 1010, the at least one optical element may modify the detected reflection in a manner accounting for a rotation of the object. At step 1012 at least one processor (e.g., processor 125) may determine an amount of rotation of the object around the at least one rotational axis based on a relative phase difference between the detected reflections and the internal reference beams.

Figure 11:
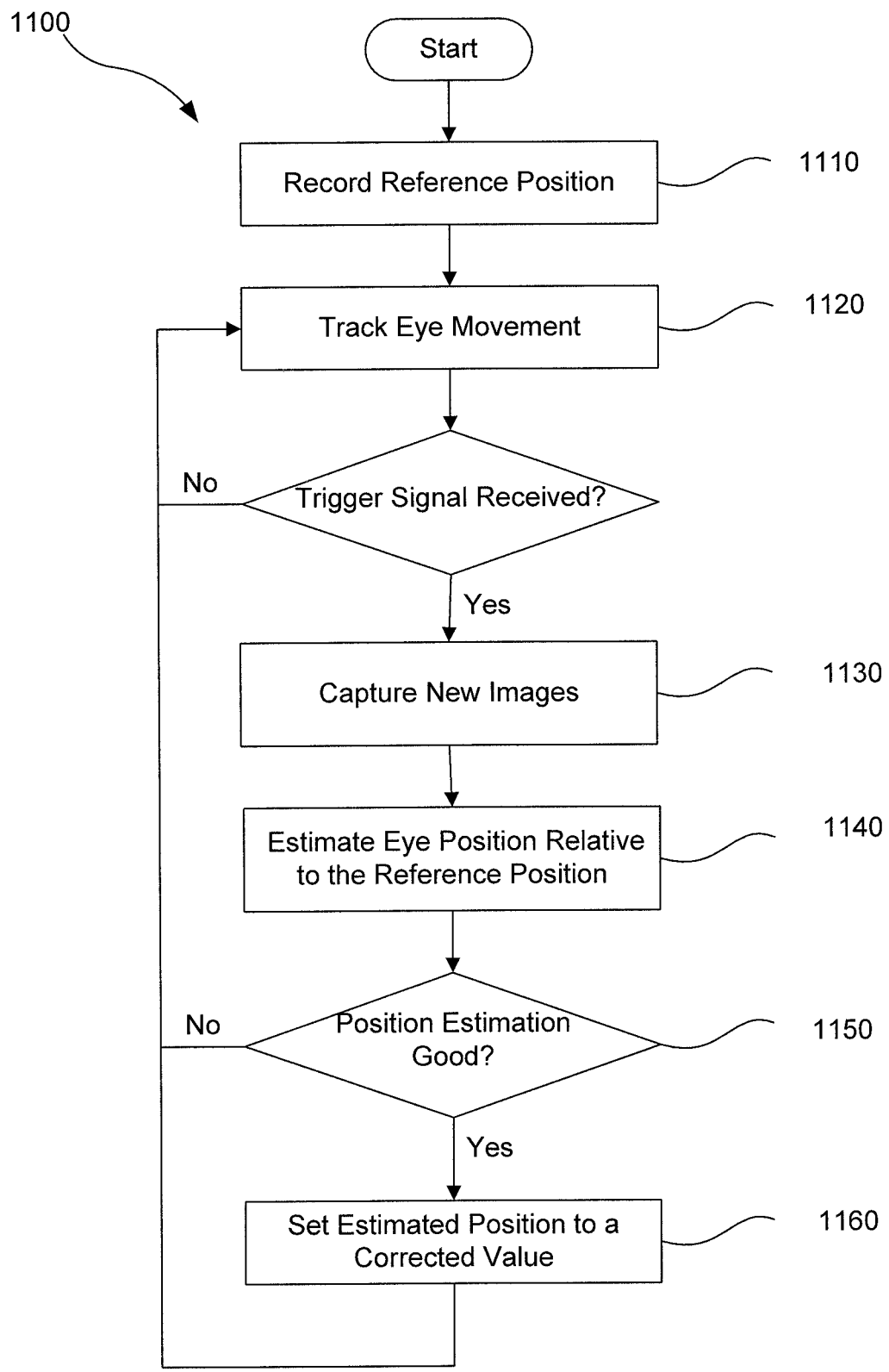
FIG. 11 is a flowchart of an exemplary method for estimating eye gaze direction, according to embodiments of the present disclosure.

Embodiments of the interferometer as described herein may be utilized in a variety of methods for tracking eye movement and for estimating gaze direction. FIG. 11 is a flowchart of an exemplary method 1100 for estimating gaze direction. Method 1100 may selectively use embodiments of interferometers and features of the embodiments of interferometers described above in reference to FIGS. 1-9. Consistent with the present disclosure, method 1100 may include steps for determining the resting position of an eye, tracking movement of the eye, and estimating the gaze direction based on tracked movement of the eye relative to the resting position. Method 400 may continuously or intermittently estimate the eye gaze direction. It will be readily appreciated that the illustrated method can be altered to modify the order of steps, delete steps, or further include additional steps, without departing from the spirit and scope of this disclosure or the innovations described herein.

In step 1110, a reference position of an eye may be determined and recorded. The reference position may include a reference direction and a reference location. In some embodiments, the reference position is the initial resting position of the eye. In one embodiment, method 1110 may use one or more imaging sensors 102 to take reference images of the sclera that show the locations of blood vessels in a few areas of the sclera when the eye is in the initial resting position.

In step 1120, movement of the eye may be continuously or intermittently tracked. For example, the amount of rotation of the eye around at least one rotational axis can be determined using embodiments of the interferometers and features of the embodiments of the interferometers described above. The position of the eye relative to the reference position in three dimensions ("the relative position of the eye") may be determined based on the tracked movement of the eye, allowing for estimating the eye gaze direction.

Upon receiving a trigger signal from the at least one processor of the interferometer, method 1100 may further include step 1130, where new images of the sclera may be periodically captured. In some embodiments, the trigger signal is time and new images of the sclera are taken every period of time, such as every second. In other embodiments, the trigger signal is a movement of the eye, such as a blink.

In step 1140, the relative position of the eye may be determined. In some embodiments, step 1140 may include comparing the new images of the sclera to the reference images of the sclera and estimating the relative position of the eye based on the comparison. The comparison may further general a quality measure for evaluating the estimated position. The relative position of the eye in three dimensions may be estimated based on the comparison.

In step 1150, the estimation of the eye position relative to the reference position is evaluated. If the estimation is not acceptable, method 1100 goes back to step 1120 to continue tracking eye movement and estimating the relative position of the eye. If the estimation is acceptable, method 1100 may optionally include step 1160. In step 1160, the estimated relative position of the eye in step 1120 is reset to a corrected value to improve the accuracy of the estimation. For example, the estimated relative position of the eye in step 1120 may be added with an offset determined based on the estimated relative position of the eye in step 1140. This reset may allow method 1100 to continue tracking the actual position of the eye with reduced accumulated errors.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

Instructions or operational steps stored by a computer-readable medium may be in the form of computer programs, program modules, or codes. As described herein, computer programs, program modules, and code based on the written description of this specification, such as those used by the controller, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An interferometer for measuring rotational movement, the interferometer comprising:
   a housing;
   a light source within the housing configured to project coherent light toward an opposing non-coded surface of a spherical object configured to rotate about at least one rotational axis;
   at least one optical element configured to modify the projected coherent light in a manner accounting for a rotation of the spherical object;
   at least one sensor within the housing including at least one light detector configured to detect reflections of the modified projected coherent light from the opposing non-coded surface as the spherical object rotates relative to the housing; and at least one processor configured to receive input from the at least one sensor and to determine an amount of rotation of the spherical object around the at least one rotational axis, wherein the amount of rotation is determined without relying on any recognizable visual features on the surface of the spherical object.

2. The interferometer of claim 1, wherein the spherical object is a spheroid configured to rotate about the at least one rotational axis that includes a first rotational axis and a second rotational axis, the at least one sensor includes at least two light detectors, and the at least one processor is configured to determine a first amount of rotation of the spherical object around the first rotational axis and a second amount of rotation of the spherical object around the second rotational axis.

3. The interferometer of claim 2, wherein the spherical object is an eye and the at least one processor is configured to track movement of the eye.

4. The interferometer of claim 3, wherein the at least one processor is further configured to transmit information indicative of a position of the eye relative to a reference position to a paired head-mounted display device for causing the paired headset to change displayed content.

5. The interferometer of claim 2, wherein the at least one optical element is configured to be located at a predefined working distance from a center of rotation of the spheroid and to include a focusing lens with a focal length corresponding to the predefined working distance.

6. The interferometer of claim 5, wherein the at least one optical element is configured to modify the projected coherent light by forming a spherical illumination wave converging to the center of rotation of the spheroid.

7. The interferometer of claim 6, further comprising a beam splitter configured to split the projected coherent light into a plurality of internal reference beams, wherein each internal reference beams is associated with a different direction.

8. The interferometer of claim 7, wherein the at least one optical element is configured to modify the detected reflections such that a resulting interference of the modified reflections with the plurality of internal reference beams is linearly related to the amount of rotation.

9. The interferometer of claim 8, wherein the at least one processor is further configured to determine the first amount of rotation of the spherical object around the first rotational axis and the second amount of rotation of the spherical object around the second rotational axis based on a non-zero phase change associated with detected reflections of the spherical illumination wave and the plurality of internal reference beams.

10. The interferometer of claim 1, wherein the at least one optical element includes a focusing lens associated with an adjustable focal point and the at least one processor is further configured to determine an offset of the adjustable focal point from a center of rotation of the spherical object, and to trigger an autofocus process.

11. The interferometer of claim 1, wherein the at least one optical element includes a beam splitter configured to split the projected coherent light into at least two beams configured to travel parallel to each other toward the spherical object.

12. The interferometer of claim 1, wherein the at least one optical element is configured to modify the projected coherent light by splitting the projected coherent light into the at least two beams for concurrently illuminating different areas of the spherical object.

13. The interferometer of claim 1, wherein the at least one processor is further configured to determine the amount of rotation of the spherical object around the at least one rotational axis without prior knowledge of a radius or a shape of the spherical object.

14. The interferometer of claim 1, wherein the at least one sensor includes at least two light detectors and the at least one processor is further configured to determine an amount of translational movement of the spherical object towards or away from the at least one sensor.

15. A head-mounted display device, the device comprising:
a housing;
a light source within the housing configured to project coherent light toward an eye of a user wearing the device;
at least one optical element configured to modify the projected coherent light in a manner accounting for a rotation of the eye;
at least one sensor within the housing including at least two pairs of light detectors and configured to detect reflections of the modified projected coherent light from the eye as the eye rotates relative to the housing;
memory configured to store a resting position of the eye; and at least one processor configured to:
display content to the user;
determine an amount of rotation of the eye around the at least one rotational axis based on a relative phase difference between the detected reflections and internal reference beams, wherein the amount of rotation is determined without relying on any recognizable visual features on the surface of the eye;
identify a position of the eye relative to the resting position; and
change the content displayed to the user in response to the identified position of the eye of the user wearing the device.

16. The head-mounted display device of claim 15, wherein, when the user wears the head-mounted display device, the at least one optical element is configured to be located between 25 mm and 50 mm from the eye of the user and a beam size associated with the modified projected coherent light is between 1 mm and 5 mm.

17. The head-mounted display device of claim 15, wherein the light source is configured to project a coherent light having a wavelength between 700 nm and 1000 nm toward the eye of the user to enable tracking a saccadic movement of eye and a fixation movement of eye.

18. The head-mounted display device of claim 15, wherein the at least one processor is further configured to determine the resting position of the eye based on reflections of the modified projected coherent light measured during a period of time.

19. The head-mounted display device of claim 15, wherein at least one optical element is configured to direct the modified projected coherent light to a location that is on a sclera of the eye closer to a corner of the eye than to a center of an iris of the eye.

20. A method for measuring rotational movement, the method comprising:
projecting coherent light toward an opposing non-coded surface of an object configured to rotate about at least one rotational axis;

splitting the projected coherent light into a plurality of internal reference beams, wherein each internal reference beams is associated with a different direction;

modifying the projected coherent light in a manner accounting for a rotation of the object;

detecting reflections of the modified projected coherent light from the opposing non-coded surface as the object rotates;

modifying the detected reflection in a manner accounting for a rotation of the object; and determining an amount of rotation of the object around the at least one rotational axis based on a relative phase difference between the detected reflections and the internal reference beams, wherein the amount of rotation is determined without relying on any recognizable visual features on the surface of the object.

21. The method of claim 20, wherein the object is a cylindroid configured to rotate about a single rotational axis and the method further includes determining an amount of rotation around the single rotational axis.

22. The method of claim 21, wherein modifying the projected coherent light in a manner accounting for the rotation of the object is using a cylindrical lens configured to be located at a predefined working distance from a center of rotation of the cylindroid and with a focal length corresponding to the predefined working distance.

23. The method of claim 22, wherein the cylindrical lens is configured to modify the projected coherent light by forming a cylindrical illumination wave converging to an axis of rotation of the cylindroid, and wherein the method further includes determining the amount of rotation around the single rotational axis based on a non-zero phase change associated with detected reflections of the cylindrical illumination wave and at least one internal reference beam.

* * * * *